(12) United States Patent
McFetridge

(10) Patent No.: US 7,775,965 B2
(45) Date of Patent: Aug. 17, 2010

(54) DECELLULARIZED GRAFTS FROM UMBILICAL CORD VESSELS AND PROCESS FOR PREPARING AND USING SAME

(75) Inventor: Peter S. McFetridge, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 1460 days.

(21) Appl. No.: 11/075,966

(22) Filed: Mar. 9, 2005

(65) Prior Publication Data
US 2005/0203636 A1   Sep. 15, 2005

Related U.S. Application Data

(60) Provisional application No. 60/551,607, filed on Mar. 9, 2004.

(51) Int. Cl.
*A61F 2/00* (2006.01)
(52) U.S. Cl. ...................... 600/36; 623/23.72
(58) Field of Classification Search .................. 600/36; 606/159; 623/1.1, 1.41, 1.43, 11.11, 23.72, 623/916; 435/307.1
See application file for complete search history.

(56) References Cited

U.S. PATENT DOCUMENTS

| | | | |
|---|---|---|---|
| 3,974,526 A | | 8/1976 | Dardik et al. |
| 3,988,782 A | | 11/1976 | Dardik et al. |
| 4,990,131 A | | 2/1991 | Dardik et al. |
| 5,131,908 A | | 7/1992 | Dardik et al. |
| 5,908,449 A | * | 6/1999 | Bruchman et al. .......... 128/898 |
| 6,291,240 B1 | * | 9/2001 | Mansbridge et al. ........ 435/395 |
| 6,376,244 B1 | * | 4/2002 | Atala .......................... 435/376 |
| 6,416,995 B1 | * | 7/2002 | Wolfinbarger ............ 435/289.1 |
| 6,479,064 B1 | * | 11/2002 | Atala .......................... 424/423 |
| 6,689,161 B2 | | 2/2004 | Chen et al. |
| 2003/0143207 A1 | * | 7/2003 | Livesey et al. ............. 424/93.7 |
| 2003/0171824 A1 | * | 9/2003 | Abraham et al. ......... 623/23.75 |
| 2004/0048796 A1 | * | 3/2004 | Hariri et al. ................... 514/12 |
| 2005/0013870 A1 | * | 1/2005 | Freyman et al. ............. 424/520 |

OTHER PUBLICATIONS

McFetridge, P. et al.; "Preparation of porcine carotid arteries for vascular tissue engineering applications"; Wiley InterScience:224-234 (2004).
Rashid, S.T. et al.; "Engineering of bypass conduits to improve patency"; Cell Prolif (37):351-366 (2004).
McFetridge, P. et al.; "Endothelial and smooth muscle cell seeding onto processed *ex vivo* arterial scaffolds using 3D vascular bioreactors"; ASAIO Journal:591-600 (2004).

* cited by examiner

*Primary Examiner*—John P Lacyk
(74) *Attorney, Agent, or Firm*—Dunlap Codding, P.C.

(57) ABSTRACT

A tissue graft is disclosed that includes a decellularized umbilical vessel having a luminal surface and an ablumenal surface, wherein the decellularized umbilical vessel is prepared by an automated dissection process. The decellularized umbilical vessel has not been substantially cross-linked. In one method of use, the decellularized umbilical vessel is capable of having at least one cell type seeded at least a portion of at least one of the luminal and ablumenal surfaces thereof. A process of preparing the tissue graft, methods of using the tissue graft, and kits which contain the tissue graft are also disclosed.

21 Claims, 20 Drawing Sheets
(6 of 20 Drawing Sheet(s) Filed in Color)

The HUV (x3) will be dissected into longitudinal sections for analysis: mechanical analysis (Mech), PicoGreen DNA quantification (PG), and paraffin embedded sections for determination of viable cells, migration analysis, and scaffold remodeling.

DECELLULARIZED GRAFTS FROM UMBILICAL CORD VESSELS AND PROCESS FOR PREPARING AND USING SAME

CROSS-REFERENCE TO RELATED APPLICATIONS

This application claims benefit under 35 U.S.C. 119(e) of U.S. provisional patent application Ser. No. 60/551,607, filed Mar. 9, 2004, entitled "TISSUE ENGINEERING VASCULAR GRAFTS USING THE UMBILICAL VEIN AS A DECELLULARIZED MATRIX AND A RAPID BIOREACTOR-BASED AUTOLOGOUS CELL SEEDING TECHNOLOGY FOR BYPASS SURGERY", which is hereby expressly incorporated herein by reference in its entirety.

STATEMENT REGARDING FEDERALLY SPONSORED RESEARCH OR DEVELOPMENT

Not applicable.

BACKGROUND OF THE INVENTION

1. Field of the Invention

The present invention relates to decellularized grafts for tissue engineering, and more particularly but not by way of limitation, to decellularized grafts from umbilical cord vessels for tissue engineering as an acellular matrix and for use with cell seeding methodology.

2. Brief Description of the Art

Vascular disease is the number one cause of death in Western societies. Current treatments are limited to reconstructive surgery where a patient's own (autologous) non-diseased vessels are relocated to bypass diseased or blocked blood vessels that would ultimately result in cardiac arrest, stroke or death.

Maintaining the flow of oxygen-rich blood to organs downstream of severely occluded blood vessels is often limited to surgically by-passing diseased sections with substitute vessels. Transplanted autologous arteries are considered the "gold standard" for small diameter replacement vessels (<6 mm), with patency rates of approximately 90% at five years. By comparison, patency rates of 25-45% over 5 years are typical with synthetic alternatives such as Dacron or expanded polytetrafluoroethylene (ePTFE). Approximately 30% of all patients requiring vascular reconstructions do not have 'autologus' vessels available for use, necessitating the use of either a synthetic conduit or a non-operative approach. Small diameter (<6 mm) vascular reconstructions have proven considerably more problematic than large diameter vessel reconstructions, where reduced diameter and low flow rates, compounded by high resistance, amplify poor biological host/graft interactions. This inability to interact successfully with recipient tissues initiates a complex set of adverse biological reactions that can be broadly grouped into thrombotic and hyperplastic responses. Autologous arterial grafts are preferred over synthetics because the latter fail due to poor biocompatibility and/or mechanical properties.

Alternative approaches to improve the current situation include the development of synthetic and biological grafts, endothelial cell seeded synthetic grafts and tissue engineering. Processed biological materials have been used clinically as vessel replacements; these include cryo-preserved and cross-linked vessels such as the saphenous and umbilical veins. A distinct and important advantage of processed biological tissues over current synthetic materials is the retention of native-like mechanical properties, where the compliance (or mechanical) matching is predictive of graft success (Seifalian et al., 1999). Further, the physical and chemical environment within these materials is inherently more conducive to native vessel remodelling processes.

The umbilical cord vein has an established record as an inert 'fixed' biomaterial. However, there are several structural limitations when the umbilical cord vein is used as a glutaraldehyde 'fixed' material. Although cryo-preserved veins are a promising option, they too are limited by supply (Dresdale et al., 1990; Fujitani et al, 1992; and Davies, 1994), and umbilical cord veins, in their current form, have not proven reliable due (primarily) to a potential for aneurysm formation. With an incidence of 33% beginning at three years and increasing with time, the HUV has not seen wide spread usage (Hasson et al., 1986; Nevelsteen et al., 1988; and Karkow et al., 1986). However, other more favorable data suggests the HUV does in actual fact out perform PTFE, with patency rates 2.1 times higher (Eickhoff et al., 1987). Dardik et al. (1982), who developed the glutaraldehyde tanned HUV graft (Dardik I et al., 1973), also reported aneurysm formation, but has remarked that due to the poor patency rates of a PTFE graft the HUV is still an "acceptable alternative to the absent or deficient autologous vein". More recently Johnson et al. (2000), have reiterated the suitability of biological grafts over synthetic alternatives, with results from a five year primary patency study of 80% for saphenous vein (SV), 56% HUV and 33% for PTFE (Johnson et al., 2000).

The use of collagen based biomaterials has traditionally necessitated a degree of tissue processing to stabilize and prevent chronic immune responses against foreign epitopes (Khor, 1997; and Schmidt et al., 2000). These treatments have been applied to the umbilical vein graft to improve its biocompatibility and mechanical strength under arterial conditions (Karkow et al., 1986; Dardik H et al., 1984; Dardik, 1990; Dardik, 1995; and Miyata et al., 1989). The mechanism of stabilization is through covalent cross-linking of the collagen fibers within the ECM, rendering the material resistant to host enzymatic degradation. The reduced immune response attributed to cross-linking has been described as a 'masking' of allogenic or xenogenic components that would otherwise be seen as foreign, resulting in chronic rejection and subsequent failure of the graft. The quandary is that chemical treatments designed to stabilize and reduce immunogenicity, often inherently cytotoxic, prevent cell migration, and as such, true functionality of the graft will never be achieved. A number of acellular collagen based matrices (not cross-linked) have been studied: vascular (Teebken et al., 2000; Courtman et al., 2000; Badylak et al., 1998; and Badylak et al., 1999), bladder augmentation (Probst et al., 2000; and Probst et al., 1997) and cardiac valves (Courtman et al., 1995; Courtman et al., 1994; and Bader et al., 1998). These are promising studies with cells migrating into and populating the matrix material, showing that cross-linking is not necessarily a vital step. However, Courtman et al. (2000) found that, despite decellularization, immunogenic proteins remained localized within the vascular graft media (not the graft periphery), concluding that immunogenic proteins "arise from proteins associated with the distinct extracellular arterial immunogenic matrix". Although these materials are promising, problems of thrombosis, neointimal hyperplasia and graft degradation have meant that translating these results into viable grafts has proven a significant hurdle.

In order to replicate the success of autologous arterial transplants, a successful prosthetic must integrate and function in a similar manner to natural arteries. It is the failure of current small diameter prosthetics to integrate appropriately with recipient tissue that initiates a number of unfavorable biologic interactions cumulating in thrombotic and hyperplastic responses that lead to graft failure (Schmidt et al, 1999). To improve the host/graft interaction, it is likely that both a competent endothelium, to serve at the blood-graft interface, and a fully developed, biocompatible vascular wall, populated with vascular smooth muscle cells (VSMC), must be present. The logic behind this approach is clear: grafts frequently fail due to poor functional integration, and therefore to improve function a biologic component must be present. It follows that if the biologic component is more comprehensive, then it is likely improved biologic function will result. As neither a functional vessel wall nor an endothelium will spontaneously develop in adult humans (at an appreciable rate), tissue engineering offers a unique methodology where replacement neo-vessels can be grown in vitro (Nikalson et al., 1999; Nerem et al., 2001; Langer et al., 2000; and L'Heureux et al., 1998). By incorporating functional cell lineages into 3D scaffolds, or blood vessel templates, improved biologic function can be achieved to minimize intrinsic host repair or defense mechanisms that would otherwise lead to the aforementioned thrombotic and hyperplastic responses.

A key component of this process is the choice of 3D scaffold with which tissue growth is guided. The list of 3D scaffold materials continues to grow, and includes the following: permanent synthetics (Deutsch et al., 1999), biodegradable synthetics (Hoerstrup et al., 2001; and Niklason et al., 1997), or variously treated ex vivo materials from either human or animal origin (Khor et al., 1997; Niklason et al., 1999; McFetridge et al., 2004; Schaner et al., 2004, and Hiles et al., 1995). The ideal vascular scaffold is required to be biocompatible and ideally have in vivo-like mechanical properties with the capacity to guide, support, and maintain cellular function. Compared to many synthetic polymers, processed ex vivo materials often lack mechanical uniformity, consistency, composition, and can be restrictive in their final shape/structure. Extraction of foreign epitopes to reduce the immunogenicity of ex vivo materials is clearly an important issue. Methods of tissue processing that extract immunogenic components have been shown to be relatively successful at reducing the immune impact of these ex vivo biomaterials (Schaner et al., 2004; and Hiles et al., 1995). The clinical use of collagen hydrogels in cosmetic surgery and the small intestinal submucosa (SIS) have validated the use of these materials (Chen et al., 2001; Hiles et al., 1995; and Lantz et al., 1993). Although ex vivo tissue processing is an effective means to reduce the immunogenic load, mass transfer limitations of thicker/larger organs are likely to reduce processing efficiency. A distinct and important advantage of ex vivo vascular derived scaffolds is that the physical and chemical environment is inherently more conducive to cell adhesion and native remodeling processes than many synthetic alternatives. For example, cell adhesion is enhanced due to endogenous RGD adhesion sequences present within the amino acid sequence of extracellular matrix (ECM) collagen (Saito et al. 2001), and the retention of the native blood vessels' mechanical properties (compliance matching) is an important predictor of graft success (Tai et al., 2000; Roeder et al., 1999; and Seifalian et al., 1999).

The human umbilical vein (HUV) has a comprehensive clinical history as a glutaraldehyde fixed bypass graft (Dardik et al., 1973; Dardik et al., 1976; Dardik et al., 1988; Dardik et al., 1976; Dardik et al., 1995; and Dardik, 2001). However, time consuming and error prone manual dissection procedures result in a lack of mechanical uniformity, limiting the use of this material as a 'stand-alone scaffold' (without additional support), as a biomaterial for tissue engineering applications. The HUV has a number of properties that show promise as an acellular 3D vascular scaffold: (1) it has the structure and form of a natural blood vessel to more closely replicate arterial compliance; (2) its allograft origin reduces the risk of interspecies viral contamination; and (3) because of its vascular derivation, it presents surfaces that are conducive to cellular attachment and subsequent remodeling processes (McFetridge et al., 2004; McFetridge, 2002; Teebken, 2004; and Teebken et al., 2000). With lengths that can exceed 500 mm and internal diameters from 4-6 mm, the HUV is appropriate for several vascular reconstructive applications.

Therefore, there exists a need in the art for new and improved biomaterials derived from ex vivo tissues that offer a viable alternative for use as tissue engineering scaffolds. It is to such a decellularized graft from an umbilical cord vessel, as well as methods of preparing and using same, that the present invention is directed.

SUMMARY OF THE PRESENT INVENTION

According to the present invention, tissue grafts for seeding cells thereon are provided. Broadly, the present invention is related to decellularized grafts from umbilical cord vessels for tissue engineering using cell seeding methodology.

An object of the present invention is to provide an acellular tissue graft matrix that includes a decellularized umbilical vessel having a luminal surface and an ablumenal surface. The decellularized umbilical vessel is prepared by an automated dissection process and is not substantially cross-linked. The umbilical vessel may be an umbilical vein or an umbilical artery, and may be from a mammal, such as but not limited to, a human.

In one embodiment of the present invention, the decellularized umbilical vessel of the tissue graft of the present invention has a burst pressure of greater than or equal to about 600 mmHg. The decellularized umbilical vessel of the tissue graft of the present invention is preferably capable of retaining at least one suture therein under an applied force. The decellularized umbilical vessel of the tissue graft of the present invention also preferably has a mechanical compliance value on a same order of magnitude as a native artery (preferably in a range of from about 4% to about 24%), and also preferably has a biphasic stress-strain relationship.

In one embodiment of the present invention, the tissue graft has a substantially uniform wall thickness in a range of from about 200 μm to about 3000 μm, preferably from about 400 μm to about 1000 μm, and more preferably from about 500 μm to about 750 μm. In another embodiment of the present invention, the tissue graft may be longitudinally dissected such that it is in a form of a sheet.

Another object of the present invention, while achieving the before-stated object, is to provide a tissue graft for seeding cells thereon, the tissue graft comprising a decellularized umbilical vessel having a luminal surface and an ablumenal surface. The decellularized umbilical vessel is prepared by an automated dissection process, and the decellularized umbilical vessel has not been substantially cross-linked such that the decellularized umbilical vessel is capable of having at least one cell type seeded at least a portion of at least one of the luminal and ablumenal surfaces thereof. The umbilical vessel may be an umbilical vein or an umbilical artery, and may be from a mammal, such as but not limited to, a human.

In one embodiment of the present invention, the decellularized umbilical vessel of the tissue graft of the present invention has a burst pressure of greater than or equal to about 200 mmHg, and at the time of implantation, preferably has a burst pressure of greater than or equal to about 600 mmHg. The decellularized umbilical vessel of the tissue graft of the present invention is preferably capable of retaining at least one suture therein under an applied force. The decellularized umbilical vessel of the tissue graft of the present invention also preferably has a mechanical compliance value on a same order of magnitude as a native artery (preferably in a range of from about 4% to about 24%), and also preferably has a biphasic stress-strain relationship.

In one embodiment of the present invention, the tissue graft has a substantially uniform wall thickness in a range of from about 200 µm to about 3000 µm, preferably from about 400 µm to about 1000 µm, and more preferably from about 500 µm to about 750 µm. In another embodiment of the present invention, the tissue graft may be longitudinally dissected such that it is in a form of a sheet.

In another embodiment of the present invention, the tissue graft may further have a suspension of collagen gel and at least one cell type. The collagen gel/at least one cell type suspension is seeded upon the decellularized umbilical vessel.

Another object of the present invention, while achieving the before-stated objects, is to provide a process of preparing a decellularized matrix on which at least one cell type may be seeded. In the process, at least a portion of an umbilical cord is provided, and an umbilical vessel of the umbilical cord is isolated by disposing a mandrel into a lumenal space of an umbilical vessel, wherein the mandrel has a diameter that is equal to or slightly greater than a diameter of the luminal space of the umbilical vessel, and wherein the mandrel is formed of a material having a low coefficient of expansion such that the mandrel does not expand or contract at a rate that is not supportive of the umbilical vessel supported thereon. The umbilical cord is then secured to the mandrel and frozen to a temperature in a range of from about −40° C. to about −150° C., preferably in a range of from about −60° C. to about −100° C., and more preferably, about −80° C. The remainder of the umbilical cord is then automatically dissected away from the isolated umbilical vessel, and the isolated, dissected umbilical vessel secured to the mandrel is thawed. Then the isolated umbilical vessel is decellularized, such as by a process selected from the group consisting of washing with hypotonic solution; mechanical removal methods such as cutting, scraping, shaking, and removal by forceps or other suitable instrument; treatment with at least one lipase, at least one protease, at least one nuclease, at least one solvent, and at least one detergent; and combinations thereof. In a preferred embodiment, the isolated umbilical vessel is decellularized by a pressure based extraction system with uniform convective flow.

The process may further comprise the step of unwinding the umbilical cord prior to securing the umbilical cord to the mandrel. The umbilical vessel may be an umbilical vein or an umbilical artery, and the umbilical cord may be obtained from a mammal, such as but not limited to, a human.

In one embodiment of the present invention, the process of the present invention further comprises the step of seeding at least one cell type on the decellularized umbilical vessel, wherein the at least one cell type is selected from the group consisting of smooth muscle cells, fibroblasts, endothelial cells, keratinocytes, myogenic cells, stem cells, muscle cells, epithelial cells, any other applicable cell type lineages, and combinations thereof. Any cell type appropriate for the tissue/organ being engineered by the methods of the present invention may be utilized in accordance with the present invention, for example but not by way of limitation, smooth muscle and endothelial cells for blood vessels and fibroblasts and keratinocytes for skin, and it is within the skill of a person having ordinary skill in the art to select the appropriate cell types that may be utilized in accordance with the present invention. The at least one cell type may be provided in the form of an at least one cell type/collagen gel suspension, the at least one cell type/collagen gel suspension is thus seeded on at least a portion of at least one surface of the decellularized umbilical vessel. For example, an endothelial cell/collagen gel suspension may be seeded on at least a portion of the lumenal surface of the umbilical vessel. In another embodiment, an at least one cell type/collagen gel suspension is seeded on at least a portion of the ablumenal surface of the umbilical vessel, and the at least one cell type of the at least one cell type/collagen gel suspension is selected from the group consisting of fibroblasts, smooth muscle cells and combinations thereof. In yet another embodiment, a gingival fibroblast/collagen gel suspension is seeded on at least a portion of the ablumenal surface of the umbilical vessel.

The process of the present invention may further comprise the step of longitudinally dissecting at least a portion of the decellularized umbilical vessel to form a substantially flat sheet of decellularized matrix.

Another object of the present invention, while achieving the before-stated objects, is to provide a process of forming a tissue graft having at least one cell type seeded thereon. A tissue biopsy comprising at least one cell type is obtained from a patient, and the at least one cell type is isolated and fractionated from the tissue biopsy. The isolated at least one cell type is mixed with a collagen gel to provide a collagen gel/cell suspension, and the collagen gel/cell suspension is then cultured with the tissue graft described herein above in a bioreactor under conditions that allow the collagen gel to contract on at least a portion of a surface of the tissue graft, thereby seeding the at least one cell type on at least a portion of the tissue graft. The tissue graft having the collagen gel/cell suspension thereon is then implanted into the patient.

Another object of the present invention, while achieving the before-stated objects, is to provide a process of forming a tissue graft. In the process, the acellular tissue graft matrix described herein above is provided and implanted in a patient in need thereof. In this process of the present invention, cells are not seeded on the acellular tissue graft matrix prior to implantation in the patient.

Another object of the present invention, while achieving the before-stated objects, is to provide a kit that includes the tissue graft described herein above, a collagen gel for mixing with at least one cell type to form a collagen gel/cell suspension, and means for culturing the collagen gel/cell suspension with the tissue graft under conditions that allow the collagen gel to contract on the tissue graft, thereby seeding the at least one cell type on the tissue graft. The kit may further contain means for mixing the collagen gel with at least one cell type to form a collagen gel/cell suspension.

Another object of the present invention, while achieving the before-stated objects, is to provide a kit that includes the acellular tissue graft matrix described herein above.

Other objects, features and advantages of the present invention will become apparent from the following detailed description when read in conjunction with the accompanying drawings and appended claims.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
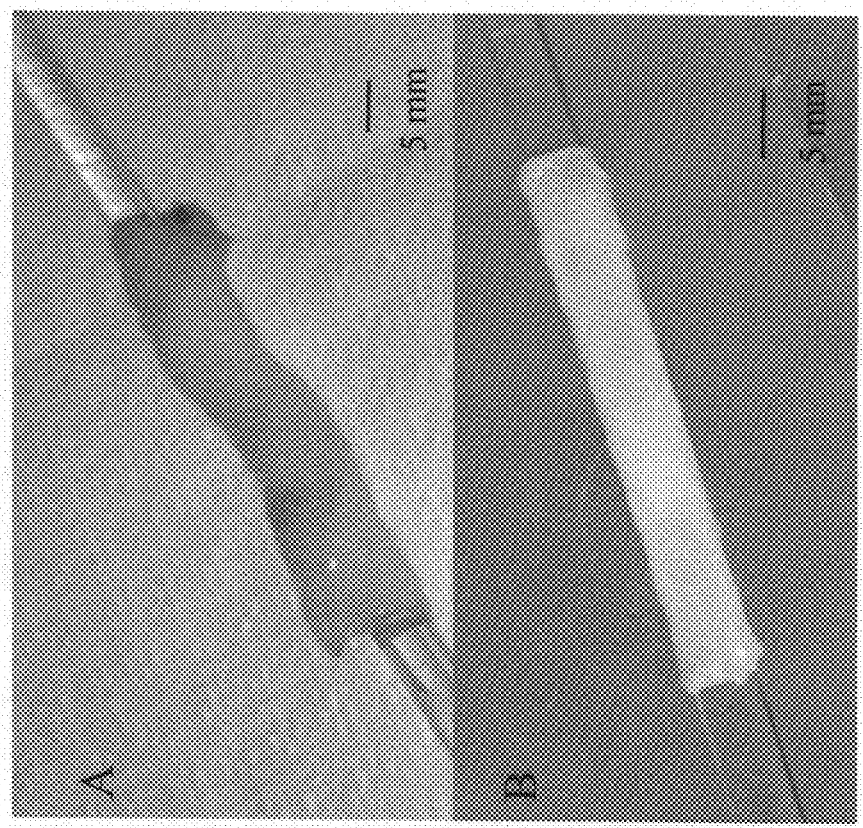
FIG. 1 contains photographs of (A) whole human umbilical cord disposed on a glass mandrel, and (B) a manually dissected human umbilical vein (mHUV) obtained from the whole human umbilical cord. The non-uniform nature of the mHUV is not desirable for a tissue engineering scaffold.

Before explaining at least one embodiment of the invention in detail by way of exemplary drawings, experimentation, results, and laboratory procedures, it is to be understood that the invention is not limited in its application to the details of construction and the arrangement of the components set forth in the following description or illustrated in the drawings, experimentation and/or results. The invention is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

The term "vascular tissue" as used herein will be understood to include a blood vessel or a portion thereof, one or more valves dissected from a blood vessel, a valve retained within a portion of a blood vessel, an aortic or pulmonary valve dissected and free of non-valvular tissue, an aortic or pulmonary valve retained within a dissected blood vessel or cardiac tissue, or any other vascular tissue. Blood vessels may include arteries and veins, portions thereof, and vascular beds containing arteries or veins.

The term "umbilical vessel" as used herein will be understood to refer to any vessel located in the umbilical cord, including an umbilical vein or an umbilical artery.

The term "decellularized" as used herein will be understood to mean that physical, chemical, or enzymatic means, or any combination thereof, has substantially or completely removed the cellular component of vascular tissue thereof. The remaining decellularized vascular tissue comprises the extracellular matrix of the native vascular tissue and may include, but is not limited to, elastin, collagen, fibrin, and other extracellular proteins or non-proteinaceous compounds found in vascular tissue, or any combination thereof known to one of ordinary skill in the art.

The terms "vascular graft", "vascular prosthesis", "vascular prostheses" or "vascular implant" are used herein interchangeably and will be understood to refer to a surgical implant or implants derived from, or inserted into, the vascular system of a human or animal patient. The term is intended to apply to surgical implants made of synthetic or natural materials or any combination thereof including, but not limited to, decellularized vascular tissue.

The terms "graft" and "prosthesis" are used herein interchangeably and will be understood to refer to any surgical implant, either derived from the tissues of the recipient patient, or from the tissues of a donor of the same or different species as the recipient. The graft or prosthesis may be fully or partially synthetic, and comprised of any suitable material well known to one of ordinary skill in the art.

The term "autologous" as used herein will be understood to refer to a graft or prosthesis of surgically implanted material obtained from a donor and reimplanted into same donor.

The term "allogenic" as used herein will be understood to refer to a graft or prosthesis of surgically implanted material obtained from a donor of one species and used in a recipient of the same species.

The term "xenogenic" as used herein will be understood to refer to a graft of surgically implanted material donated by an animal of one species and implanted into a recipient animal of another species. Donor species may include, but are not limited to pigs, sheep, cows, various primate species, humans, and any genetically modified variants thereof.

The terms "protease" or "peptidase" are used herein to refer to any enzyme capable of digesting a protein to peptides or a peptide to its constituent amino acids. Examples of proteases used in accordance with the present invention include, but are not limited to, trypsin, proteinase K, or any other protease or peptidase that is known to one of ordinary skill in the art.

The term "lipase" as used herein refers to any enzyme, modified enzyme or combinations thereof that is capable of digesting lipids. Lipases are known to one of ordinary skill in the art and therefore no further description of lipases is considered necessary herein.

The term "nuclease" as used herein refers to an enzyme or chemical procedure or combination thereof that will specifically degrade and destroy nucleic acids. Examples of nucleases that may be utilized in accordance with the present invention include, but are not limited to, deoxyribonuclease (DNAse), ribonuclease (RNAse), micrococcal nuclease, exonuclease III, S1 nuclease, or any other nuclease known to one of ordinary skill in the art.

The term "solvent" as used herein will be understood to refer to any liquid compound or composition that dissolves or is capable of dissolving another component. Examples of solvents that may be utilized in accordance with the present invention include but are not limited to, ethanol, butanol, water, combinations thereof, and the like.

The term "detergent" as used herein refers to any compound or composition that is capable of solubilizing and extracting lipids from tissue. Examples of detergents that may be utilized in accordance with the present invention include, but are not limited to, Triton X-100, sodium dodecyl sulfate (SDS), sodium lauryl sulfate (SLS), or any other detergent or combination thereof known to one of ordinary skill in the art.

A small diameter vascular bypass grafting material that is biocompatible with appropriate mechanical properties, and is resistant to thrombosis and hyperplastic responses, is yet to be found. The use of ex vivo blood vessels as scaffolds for guided organ regeneration aim to provide an ideal chemical and physical environment for improved biological function and integration. The use of these ex vivo tissues does, however, necessitate a degree of tissue processing to stabilize, sterilize, and prevent a chronic foreign body response (Khor, 1997; and Schmidt et al., 2000). Two approaches have generally been taken: (1) cross-linking and/or (2) removal of host epitopes by decellularization. The tanning, or glutaraldehyde treatment, that improves long-term stability and reduces immune reactivity, does so by forming chemical cross-links in the extracellular matrix (ECM) that stabilizes the structure and creates a barrier for cellular infiltration (Courtman et al., 2001). The inherent drawbacks of 'fixed' or 'cross-linked' materials is that they often retain cytotoxic compounds from the cross-linking (Hasson et al., 1986), and are generally incapable of cellular remodeling. As such these materials remain physiologically inert, behaving much like an synthetic material that cannot respond to changes in its environment (Miyata et al., 1989). The glutaraldehyde tanned human umbilical vein graft developed by Dardik et al., (not specifically decellularized) is an effective alternative to poorly performing current synthetic materials for small diameter vascular reconstructions (Dardik I et al., 1973; Dardik H et al., 1988; Dardik H, 1995; and Johnson et al., 2000). However, like other cross-linked and permanent synthetic materials, remodeling to form a functional vessel cannot occur.

To avoid cross-linking, the material must be tolerated by the recipient's immune system and withstand prolonged exposure to the stresses of in vivo arterial hemodynamics. As such, the success of ex vivo materials is dependent on the scaffold of choice and the pre-implantation processing methodologies to ensure longevity, immunological acceptance and graft sterility. The list of methods used to prepare ex vivo materials is rapidly expanding; these include, osmotic shock (Mechanic, 1992; and Probst et al., 1997), acids (Probst et al., 1997; and Badylak et al., 1998), bases (Goissis et al., 2000), detergents (Bodnar et al., 1986; Tamura et al., 1999; Courtman et al., 1994; and Gamba et al., 2002), enzymes (McFetridge et al., 2004; Teebken et al., 2000; Gamba et al., 2002; Oliver et al., 1985; and Bader et al., 1998), solvents (Goissis et al., 2000; Oliver et al., 1985; Malone et al., 1984; Vyavahare et al., 1997; and Reid et al., 1987), with numerous tissues and organs being decellularized including: vascular (Teebken et al., 2000; Courtman et al., 2001; Badylak et al., 1998; Courtman et al., 2001; and Badlak et al., 1999), bladder (Probst et al., 1997; and Probst et al., 2000), cardiac valves (Courtman et al., 1994; Bader et al., 1998; and Courtman et al., 1995), and others (Kwon et al., 2002; and Badylak, 2004). Several of these studies have shown cells migrating into and populating the matrix material, indicating that cross-linking is not necessarily a vital step. However, Courtman et al (2001) found that, despite decellularization, immunogenic proteins remained localized within the media of the vascular graft (not the graft periphery), concluding that immunogenic proteins arise from proteins associated with the distinct extracellular arterial matrix (Courtman et al., 2001). It is plausible however that mass transfer limitations increase as tissue size increases, resulting in a reduced efficiency of extraction procedures to remove immunogenic residues that lie in the center of the matrix. The development of technologies to limit mass-transfer effects using pressure gradients during tissue processing may improve extraction procedures and thus prove valuable in the development of acellular scaffolds.

Traditionally discarded after division from the infant at birth, the umbilical cord is composed of a vein and two arteries surrounded by a sticky, jelly-like substance called Wharton's jelly, all encased in the surrounding tissue. The cord varies in length from inches to over three feet in length and is highly flexible. Both the arteries and veins contained therein are suitable for use in vascular surgery. The umbilical cord is fetal tissue in a primitive state, giving it the advantage that antigenicity is lower than in adult tissue.

The umbilical cord may be used fresh, or it may be preserved for future use. The cord may be freeze-dried, refrigerated, chemically stored or preserved in other known ways. It may require treatment with antibiotics, chemicals, drugs, X-rays and temperature to ensure that it is sterile when ready for use. It is antigenic and may require chemical or other known treatment to remove any antigen substances. Coiled at the time of delivery, the cord can be straightened out by mechanical or chemical techniques. Cords obtained from mammals, premature babies, early or terminated pregnancies can also be used to repair smaller vessels. It should be noted that the availability of umbilical cords represents a virtually unlimited supply of grafting material in connection with the present invention.

Therefore, the present invention is directed to a tissue graft composition comprising an umbilical vessel prepared by an automated dissection procedure, as well as methods of preparing and using same. In the automated dissection method of the present invention, an umbilical vessel can be extracted from the umbilical cord in a maximum of about 2 minutes, producing a mechanically uniform material (Daniel et al., 2004; McFetridge et al., 2004; and Daniel et al., 2004). Briefly, the method of the present invention involves inserting a mandrel through the lumen of the umbilical vessel and securing the vessel to the mandrel, followed by progressively freezing the vessel to a temperature in a range of from about −20° C. to about −190° C., and preferably in a range of from about 40° C. to about −150° C., and more preferably in a range of from about −60° C. to about −100° C., and most preferably at a temperature of about −80° C. The mandrel with umbilical cord disposed thereon is then inserted into a lathe and spun. Using a low-torque cutting tool, the vessel is 'turned out' from the umbilical cord in less than about 60 seconds. This method allows for a 'dialed-in' cutting depth that is set specifically by the lathe operator, with specified wall thicknesses from 200 μm to 3000 μm. By controlling the cutting depth, only the intima and media may be retained, or by decreasing the cutting depth more of the hyaluronic acid-rich extracellular matrix (ECM) that surrounds the vein media may be incorporated. Achieving a minimal wall thickness of the dissected vessel is important, as a thickness thin enough to enable cell-cell communication between cells seeded on the ablumenal surface and cells seeded on the luminal surface will speed graft development.

In the automated dissection procedure for preparing the tissue graft, optimization of parameters such as mandrel size, type and composition; temperature (i.e., temperatures at freezing, cutting and thawing); cord tension and twisting; the shape of the cutting tool; and the rotational speed during dissection are required to minimize damage to the umbilical vessel. For example, it is essential that the diameter of the mandrel be sufficiently large enough to stretch the vessel circumferentially to avoid variation in cutting depth, while avoiding over-stretching and potential fracturing during the freezing process. Further, due to the spiraling anatomy of the vein within the cord, is is necessary to unwind and longitudinally tension the cord to secure the vein in the correct position. Failure to do so resulted in significant variation in mechanical properties.

Thermal expansion of the mandrel during the freezing/thawing process is also considered as a potential cause of applied stress to the scaffold. If the mandrel expands or contracts at a rate that is not supportive of the tissue disposed thereon, fracturing or loss of support will result. Therefore, the mandrel utilized in accordance with the methods of the present invention must be formed of a material that has a low coefficient of expansion and is unlikely to result in significant fracturing due to expansion or contraction. Examples of materials from which the mandrel may be produced include, but are not limited to, stainless steel, plastic polymers, and combinations, laminations or modifications thereof.

The tissue graft of the present invention must have mechanical redundancy, which is critical for long-term resilience to physiological stresses (Nerem, 2000). In one embodiment of the present invention, the tissue graft should have a burst pressure of equal to or greater than about 200 mmHg, and a burst pressure of equal to or greater than about 600 mmHg at the time of implantation. The auto-dissected human umbilical vein (aHUV) of Example 1 described herein below has a burst pressure of 1082±113.4 mmHg. This is a suitable level of redundancy.

The tissue graft of the present invention must also be able to retain sutures under applied force. In Example 1 provided below, the ability of the tissue graft of the present invention to retain sutures under applied force was shown to be greater than comparable PGA scaffolds deemed acceptable for vascular grafts (Hoerstrup et al., 2001; and Niklason et al., 1999).

The tissue graft of the present invention must retain mechanical compliance values in the same order as native arteries and preserve the biphasic stress-strain relationship associated with natural blood vessels (Roeder et al., 1999), as shown herein below in Example 1. Appropriate compliance matching between host artery and prosthetic graft are important to prevent arterial hypertrophy due to increased local stress at anastomoses (Seifalian et al., 1999). As such, the ideal graft has a compliance value similar to that of the original vessel. Arndt et al. reported a compliance value of 14.7% for the human carotid under normal arterial pressure (Arndt et al., 1968). Importantly, vessel compliance decreases dramatically with age, with a loss of up to 60% compliance between ages 30 and 90, adding to the variability of compliance matching within the expected age range of the patient (Seifalian et al., 1999). Synthetic based polymers often have significantly lower compliance values compared to natural vessels (Tai et al., 2000; and Roeder et al., 1999), with a compliance value of 0.64% for PTFE (Sawyer, 1987). However, the ex vivo porcine SIS has a compliance value of 4.6% (Roeder et al., 1999), with the dHUV resulting in a compliance value of 5.7±1.3%. Importantly the compliance values for PTFE are two orders of magnitude lower than the human carotid, while ex vivo materials are more comparable to natural 'unprocessed' blood vessels.

An important consideration with regard to compliance and scaffold choice is the change in lumenal surface area through diastolic and systolic pressures. Although the diameter changes, the surface area of natural blood vessels does not significantly increase as the cardiac cycle progresses. This is due to the naturally convoluted basement membrane (BM), that allows the vessel to expand and contract without excessive stretching. By not overly stretching the BM, the adhered endothelium can maintain a competent lining. Recent evidence has shown the importance of mechanically matching the prosthetic with the patient's vessel to minimize hyperplastic responses (Seifalian et al., 1999). As such, synthetics were designed with increased compliance. If these vessels are designed to promote the development of a competent endothelium and generate native-like compliance through the cardiac cycle, a convoluted lumenal surface is necessary to prevent over-stretching of adhered cells. The likely result is exposure of the prosthetic surface to blood clotting agents during systolic pressures and the potential for thrombosis formation and eventual failure.

In one embodiment of the present invention, the method of the present invention further includes decellularizing the auto-dissected tissue graft so that the tissue graft is rendered substantially immunologically inert by removing components that may otherwise elicit an immune response. In a preferred embodiment of the present invention, decellularization is achieved by employing a pressure based extraction system where uniform convective flow is used. However, the present invention is not limited to decellularization by this method. Rather, the methods of the present invention include decellularization of the auto-dissected umbilical vessel by any physical, chemical and/or enzymatic methods of decellularization known in the art, including but not limited to, washing with hypotonic solution; mechanical removal methods such as cutting, scraping, shaking, and removal by forceps or other suitable instrument; treatment with at least one lipase, at least one protease, at least one nuclease, at least one solvent, and at least one detergent; and combinations thereof. For example, particular methods of decellularizing tissue that may be utilized in accordance with the present invention are described in U.S. Pat. No. 6,689,161, issued to Chen et al. on Feb. 10, 2004, the contents of which are hereby expressly incorporated herein by reference.

In a preferred embodiment of the present invention, the HUV is decellularized using SDS and ethanol using the pressure based extraction system with uniform convective flow. SDS and ethanol were chosen as representative mechanisms to decellularize the HUV in order to assess its capacity to undergo tissue processing without altering the vessel's mechanical (or gross biological) attributes. Although a distinct morphological change in ECM structure was noted, no significant difference was found in mechanical compliance, burst pressure, or suture retention between the automated dissection method (aHUV) and the decellularized aHUV (dHUV) of the present invention, as described in detail herein below in Example 1. Under these conditions the non-crosslinked HUV-scaffold (HUVS) of the present invention has demonstrated appropriate mechanical characteristics for use as a degradable scaffold in tissue engineering applications.

The present invention provides a biocompatible, cell adhesive ex vivo material that has improved mechanical uniformity. By preparing the HUV with a minimal wall thickness, it is envisioned that seeded VSMC and EC (on their respective surfaces) will be within cell-cell communication range (~250 µm) (Francis et al., 1997) near the point of seeding to speed graft development. Preliminary assessment of cell attachment to the HUVS of the present invention has shown hVSMC adhesion and maintenance over 7 day culture periods. Further, hVSMC have shown the capacity to migrate from the ablumenal surface toward the lumenal surface of the HUVS. The ability of hVSMC to migrate through the dense concentric layers of the ECM of the HUVS suggests a rapid remodeling potential of this material. This is not only advantageous because cellular remodeling optimizes the physical properties, but also because cellular remodeling will promote biological function and minimize degradation from host bodily fluids (Campbell et al., 1999; and Budd et al., 1991). As such, the modified HUVS of the present invention has the necessary properties for use as a scaffold for small diameter prosthetic grafts. For example, in one embodiment, the HUVS developed is aimed primarily at vascular reconstructive surgery.

The present invention also includes methods of using the tissue graft composition described herein. For vascular reconstructive surgery, at least one of fibroblast and smooth muscle cells is seeded on an ablumenal surface of the umbilical vessel scaffold, and it may further be desirable to seed endothelial cells on a luminal surface of the umbilical vessel scaffold. Cells may be seeded on the auto-dissected, decellularized umbilical vessel by any methods known in the art; however, due to the three-dimensional nature of tubular scaffolds, it previously has been very difficult to seed a surface of a tubular scaffold with a high density of cells in a uniform layer. Therefore, in one embodiment of the present invention, the cells of interest may be mixed with a collagen hydrogel to form a collagen hydrogel/cell suspension, which is allowed to adhere and absorb to the umbilical vessel scaffold. In this manner, more uniform layers of cells are achieved. The cells are then allowed to proliferate on the absorbed surface and migrate into the umbilical vessel graft. By preparing the graft with a minimal wall thickness, the cells seeded on the ablumenal surface and the cells seeded on the luminal surface of the graft should be within cell-cell communication range (~250 µm) upon minimal migration into the graft near the point of seeding, thus speeding graft development.

The cells utilized in the above-described method may be autologous cells obtained from the patient requiring vascular reconstructive surgery. Fibroblast, smooth muscle and/or endothelial cells may be obtained from a tissue biopsy (comprising vein and adipose tissue), and the cells isolated and fractionated, followed by preparation of a collagen hydrogel/cell suspension. The tissue graft construct is first cultured with the collagen gel/fibroblast and/or smooth muscle cell suspension to allow gel contraction on the tissue graft construct, and the culture period is in a range of from about 12 hours to about 120 hours, and preferably about 24 hours. Then, isolated microvascular endothelical cells are cultured with the tissue graft construct to allow seeding of the cells on the lumenal surface of the tissue graft construct. This second culture step is in a range of from about 12 hours to about 120 hours, and preferably in a range of from about 24 hours to about 48 hours. At this point, the construct having cells seeded on both surfaces thereof is prepared for implantation in the patient. By this method, the tissue engineered graft is ready for implantation in the patient in about three to four days from patient diagnosis.

While the tissue graft of the present invention is described herein previously for use in vascular reconstructive surgery, it is to be understood that the tissue graft of the present invention is not limited to such use. The present invention also includes other methods of using the tissue graft described herein. In another embodiment, the HUV is developed for use in periodontal guided tissue regeneration. Periodontal disease is a chronic mixed bacterial infection leading to a progressive loss of bone and soft tissue support of the teeth. This disease process is the major cause of tooth loss in adults. Current treatments largely focus on mechanical removal of bacteria and their products from affected tooth surfaces. Surgical techniques, such as guided tissue regeneration, are often employed in an attempt to regenerate periodontal hard and soft tissues. These techniques typically utilize some sort of physical barrier that is interposed between the soft oral tissues and the underlying tooth and bone, in order to provide a protected wound healing environment. A variety of materials have been used as physical barriers, the first being expanded polytetrafluoroethylene (e-PTFE, GORE-TX™), an inert material with a long history of use in medical applications. Although the biologic feasibility of periodontal regeneration has been clearly shown, these clinical procedures are often less than predictable, generally due to adverse soft tissue response to the materials used and/or bacterial contamination during the healing phase post surgery. The biological requirements for periodontal regeneration are not yet completely understood and the ideal materials to achieve this have yet to be developed. The use of a uniquely prepared bioscaffold derived from HUV, as described herein, overcomes the disadvantages and defects of the prior art. The unique functionality of this bioscaffold can be attributed, in part, to its multilayered composite structure, where unique properties of the vascular wall are utilized to promote wound repair. In order to fully integrate and guide tissue repair, cells from either the wound-site or from a seeded autologous source need to interact in a positive fashion with the implanted bioscaffold.

In addition to the uses described herein, it is to be understood that other uses of the tissue graft of the present invention are also within the scope of the present invention, including but not limited to, urinary tract repair, small tissue patches for wound repair, nerve regeneration, cosmetic surgery such as nasal repair, and the like. While the seeding of smooth muscle, fibroblast and endothelial cells have been described herein, it will be understood that other cell types may be seeded on the tissue graft in accordance with the present invention, based upon the method of use desired, and therefore the present invention is not limited to seeding smooth muscle, fibroblast and/or endothelial cells thereon, but rather includes the seeding of any cell type required to generate a desired tissue. Examples of other cell types that may be seeded on the tissue graft of the present invention include, but are not limited to, gingival fibroblast cells (for periodontal repair), dendritic cells (for nerve regeneration), keratinocytes, myogenic cells, stem cells, muscle cells, epithelial cells, and any other applicable cell type lineage, as well as combinations thereof.

Another embodiment of the present invention involves the utilization of the tissue graft described herein as a human model to assess metastatic activity. As the tissue graft of the present invention has been shown to have burst pressures, mechanical compliance values and biphasic stress-strain relationships comparable to that of naturally occurring blood vessels, and as smooth muscle and endothelial cells have been shown to migrate through the tissue graft of the present invention, it holds that the tissue graft of the present invention is an excellent tool for studying the ability of metastasized cancer cells to migrate through vascular tissue. Thus, a cell migration assay utilizing the tissue graft of the present invention is also within the scope of the present invention.

In addition, other model systems could be generated using the tissue graft of the present invention. For example, the tissue graft of the present invention may be utilized to study bacterial infiltration and/or biofilm formation in human tissues, such as but not limited to, oral tissues affected by periodontal disease.

The invention is further illustrated by the following examples, which are not to be construed in any way as imposing limitations upon the scope of the present invention. On the contrary, it is to be clearly understood that various other embodiments, modifications, and equivalents thereof, after reading the description herein in conjunction with the Drawings and appended claims, may suggest themselves to those skilled in the art without departing from the spirit and scope of the presently disclosed and claimed invention.

EXAMPLE 1

FIG. 1 illustrates a whole human umbilical cord (FIG. 1A), and an umbilical vein obtained from the umbilical cord by a manual dissection procedure of the prior art (FIG. 1B). Typically, manual dissection methods require about one to about three hours to produce one viable vessel, and extensive mechanical variation is displayed across the manually dissected vein. These tedious and error prone dissection methods of the prior art have restricted the veins application, unless the vessel is extensively cross-linked and reinforced with synthetic polymers (Dardik et al., 1988; and Dardik, 1995).

Figure 2:
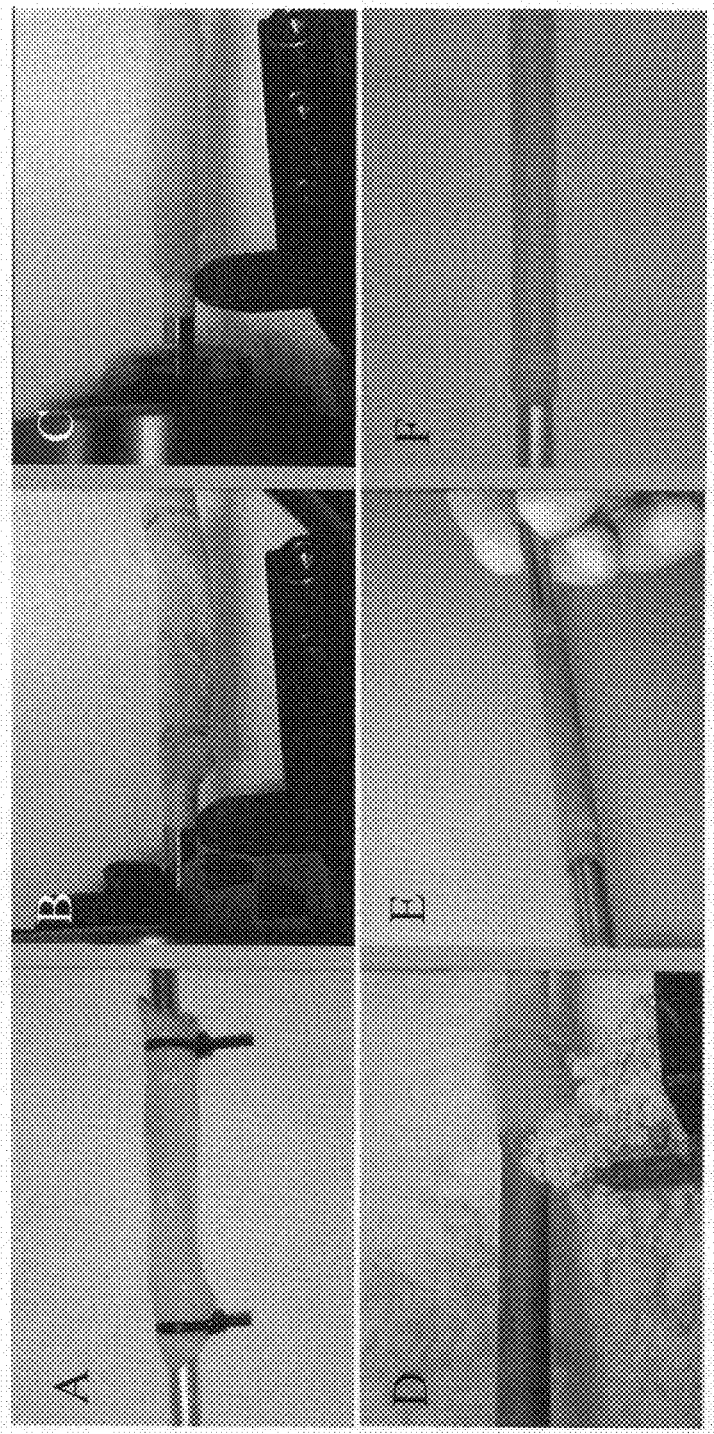
FIG. 2 illustrates a method of preparing a human umbilical vein (HUV) by auto-dissection in accordance with the present invention. Whole human umbilical cord is mounted on a stainless steel mandrel (A) and frozen to a predetermined temperature. The cord is then placed in a lathe (B), and the cutting tool transverses the section (C-D), leaving a smooth and substantially uniform scaffold (E). The frozen section is then thawed for use (F).

FIG. 2 illustrates the unique automated dissection method of the present invention. Using the automated dissection method of the present invention, an umbilical vein can be extracted from the umbilical cord in a maximum of about 2 minutes, producing a mechanically uniform material (Daniel et al., 2004; McFetridge et al., 2004; and Daniel et al., 2004). Briefly, the method of the present invention involves inserting a mandrel through the lumen of the umbilical vein and securing the vein to the mandrel (FIG. 2A), followed by progressively freezing the vein to a temperature of about −80° C. The mandrel with associated HUV is then inserted into a modified lathe (FIG. 2B) and spun at 3900 rpm. Using a low-torque cutting tool, the vein is 'turned out' from the umbilical cord in less than about 60 seconds (FIGS. 2C-E). This method allows for a 'dialed-in' cutting depth that is set specifically by the lathe operator, with specified wall thicknesses from 200 µm to 3000 µm. By controlling the cutting depth, only the intima and media may be retained, or by decreasing the cutting depth, more of the hyaluronic acid-rich extracellular matrix (ECM) that surrounds the vein media may be incorporated.

Figure 3:
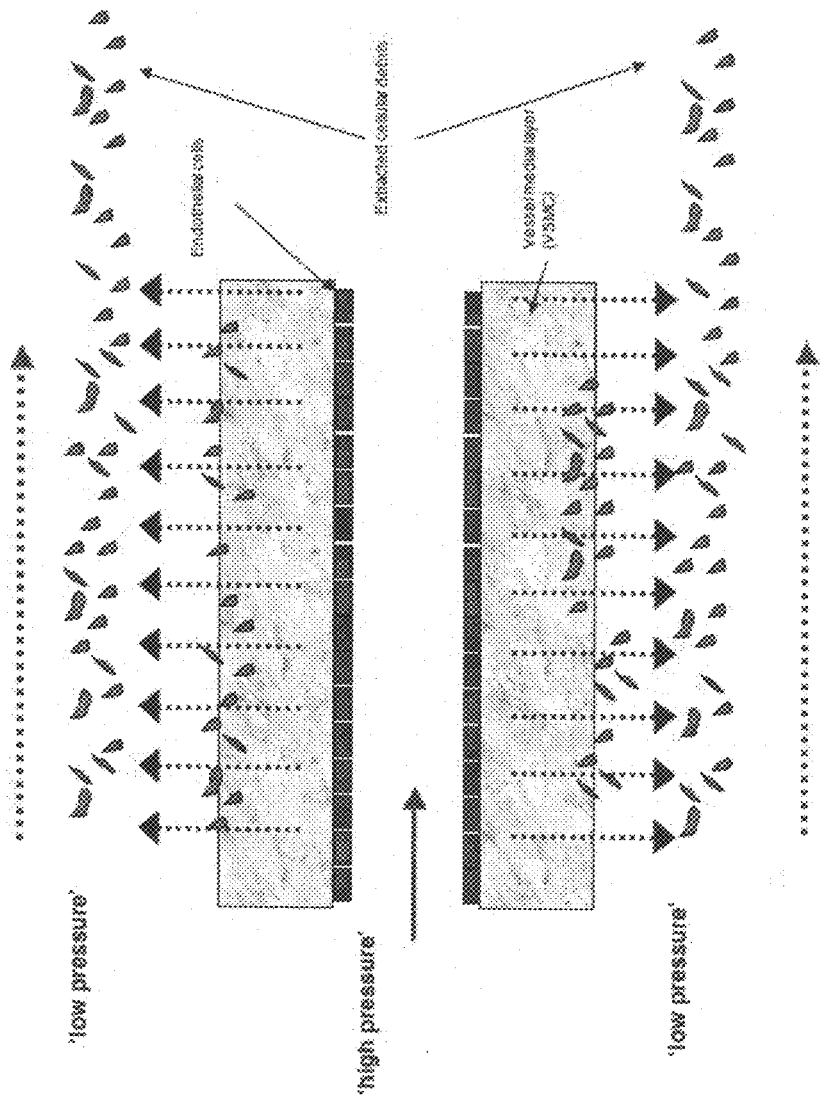
FIG. 3 graphically illustrates one method of decellularization that may be utilized in accordance with the present invention. The decellularization method is referred to as uniform convective flow, and it has been shown to increase lipid extraction by 50% compared to shaker/static systems over time.

Following auto-dissection, the tissue graft is decellularized. The inventor's studies using porcine carotid arteries have established methodologies to strip cells, and non-structural components from ex vivo tissues, without overtly damaging the artery or vein's native mechanical characteristics (McFetridge et al., 2004). The ex vivo material is rendered substantially immunologically inert by removing components that may otherwise elicit an immune response. Enhanced decellularization is achieved by employing a pressure based extraction system where uniform convective flow (rather than rinsed in a shaker bath) is used to increase non-ECM component extraction and provide improved uniformity, as well as to achieve a substantial decrease in the overall time-frame of tissue preparation. FIG. 3 diagrammatically shows the principle behind uniform convective flow. Although methods to extract cellular components from tissue have been extensively studied and proven successful, this novel method will further improve biocompatibility by active extraction.

Figure 4:
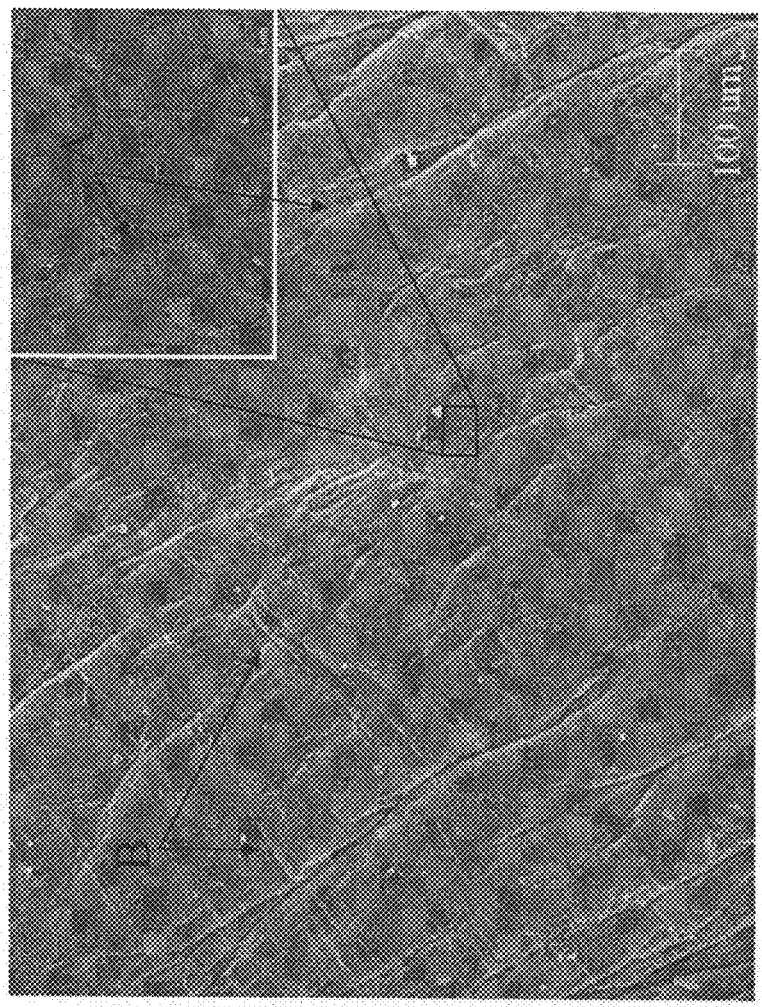
FIG. 4 illustrates scanning electron microscope (SEM) images of a lumenal surface of the auto-dissected human umbilical vein (aHUV) produced by the method of FIG. 2. The lumenal surface maintains folds of the internal elastic lamella after automated dissection (A). Striations are observed in the direction of cutting (B). No visual cracking of the lumen was observed.
Figure 5:
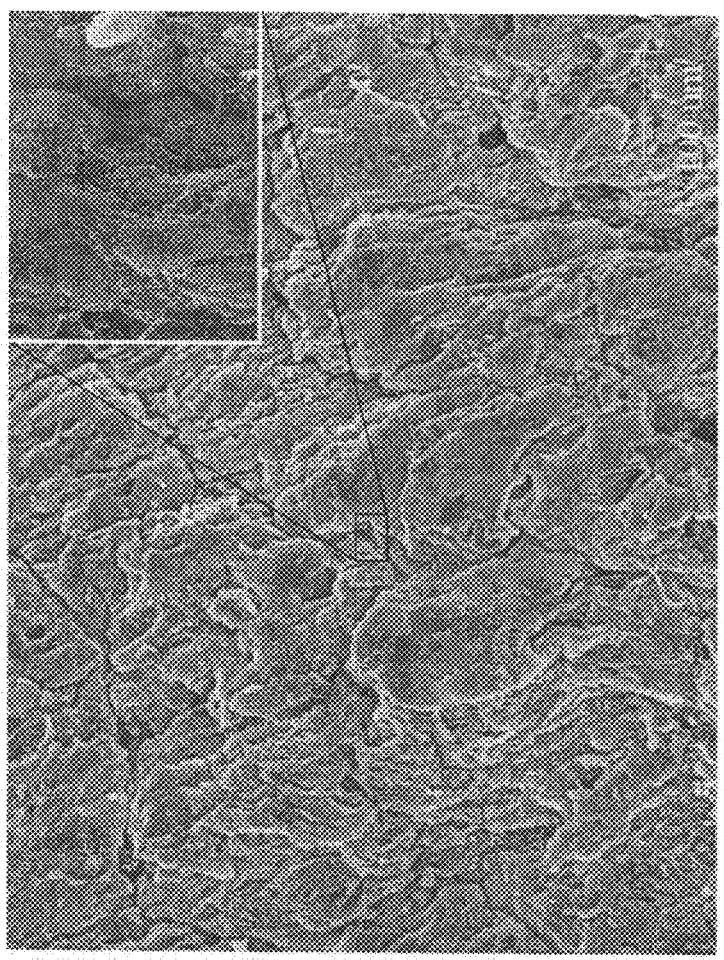
FIG. 5 illustrates SEM images of an ablumenal surface of the aHUV produced by the method of FIG. 2. The ablumenal surface maintains its fibral structure and proaminoglycans for cellular attachment after automated dissection.

SEM images of the decellularized HUV (dHUV) lumenal and ablumenal surfaces were shown to be free of whole cells, although debris fragments are noted. The lumenal surface (FIG. 4) displays the typical convoluted basement membrane (see 'A' in inset). Grooves are observed perpendicular to the longitudinal direction of the vein (labeled as 'B'); these appear to result from rotational slippage of the HUV lumen on the outer surface of the mandrel during the automated dissection process. The structure of the type I collagen ablumenal surface shown in FIG. 5 is significantly different than that of the type IV collagen typical of basement membranes on the lumenal surface (FIG. 4). The fibrous (cell free) collagen fibers of the ablumenal surface are detailed in the inset of FIG. 5.

Results from the burst pressure analyses varied significantly depending on the freezing temperature of the umbilical cord, the configuration of the mandrel, and the method of mounting the umbilical cord onto the mandrel. Freezing was required to increase vessel 'hardness' and allow a uniform dissection. A balance between tearing the tissue (not hard enough) and fracturing the tissue (too brittle) was essential. The high-speed rotary cutting technique required the cord (supported on an appropriate mandrel) to be in close contact with the underlying mandrel. Small gaps due to the vein's twisted morphology resulted in non-uniform wall thickness (data not shown), so later sections were longitudinally stretched over the mandrel and secured using nylon zip-ties to minimize 'gaps' between the mandrel and lumenal surface. Of the freezing temperatures assessed (−20, −80, and −196° C.), cords frozen to a final temperature of −20° C. were too soft for cutting, resulting in the cutting tool tearing rather than precise excision. Due to the tearing action and resulting lack of tissue uniformity, this protocol was rejected. Freezing in liquid nitrogen to a temperature of −196° C. (whether via direct plunging or progressively by prior freezing to −80° C.) resulted in gross fracturing and complete loss of containment (data not shown). This was attributed to the collagen of the umbilical cord being pre-stressed over the mandrel and passing below its glass transition temperature (Pegg et al., 1997). This method was also rejected from further analysis. Only sections frozen to −80° C. prior to excision maintained their gross mechanical attributes, allowing further analysis.

Figure 6:
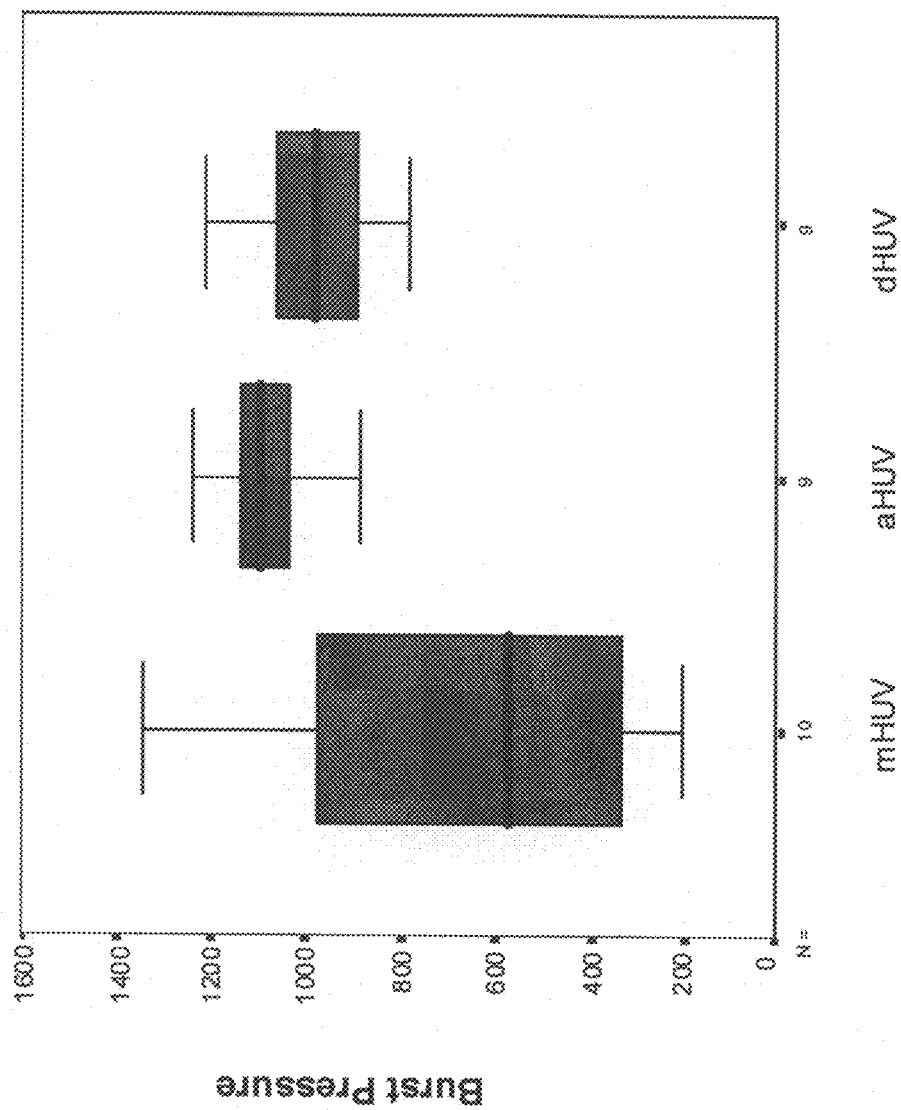
FIG. 6 graphically illustrates the burst pressures of the aHUV compared to mHUV and decellularized HUV (dHUV). The burst pressure of aHUV was significantly higher than that of the mHUV. There is a dramatic drop in both range and variance associated with automated dissection.

Burst pressure is a useful test measurement because it determines the failure of a vessel at its weakest point. In this aspect, the HUV bioscaffold has proven resilient. Burst pressure analysis dramatically illustrates the significant reduction in mechanical variation, with mean burst pressure values >1000 mmHg. Using a stainless steel (SS) tube (4 mm ID/6 mm OD) as the support mandrel, with vessels frozen to −80° C., burst pressure results were 1082.0±113.4 mmHg, significantly higher compared to that of mHUV segments (p=0.01) (FIG. 6). After decellularization, mean burst pressure values decreased to 972.8±133.8 mmHg (FIG. 6). For comparison, the mean burst pressures of presently used materials are as follows: saphenous vein, 984 mmHg; SIS, 2069-4654 mmHg; PTFE, 2590-3626; and GORE-TEX™, 600 mmHg.

Figure 7:
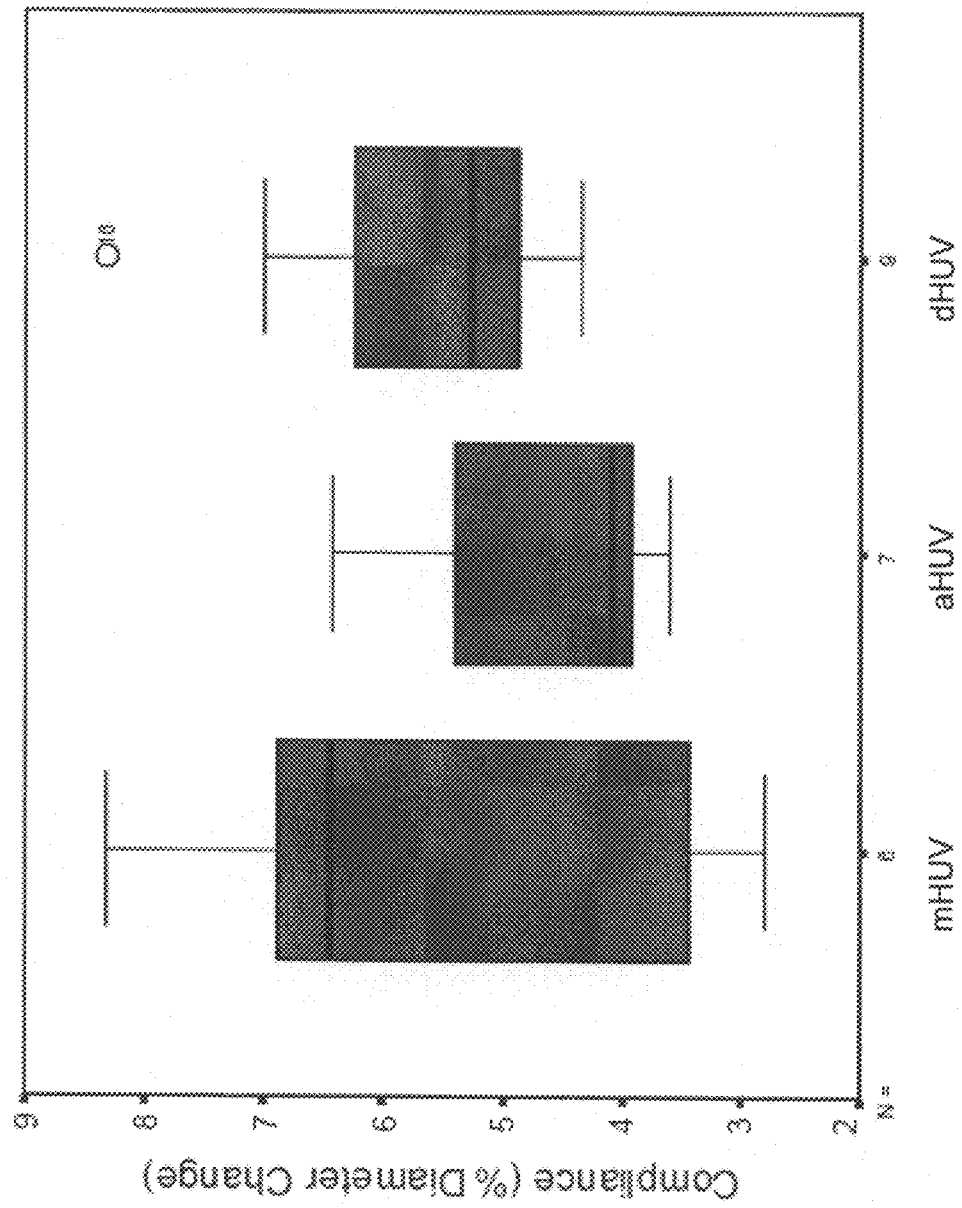
FIG. 7 graphically illustrates compliance values of mHUV, aHUV, and dHUV. Compliance is a measure of the relationship between vessel expansion and applied internal pressure. No significant difference is associated between dissection methodologies, but range and variance is greatly reduced with automated dissection.
Figure 9:
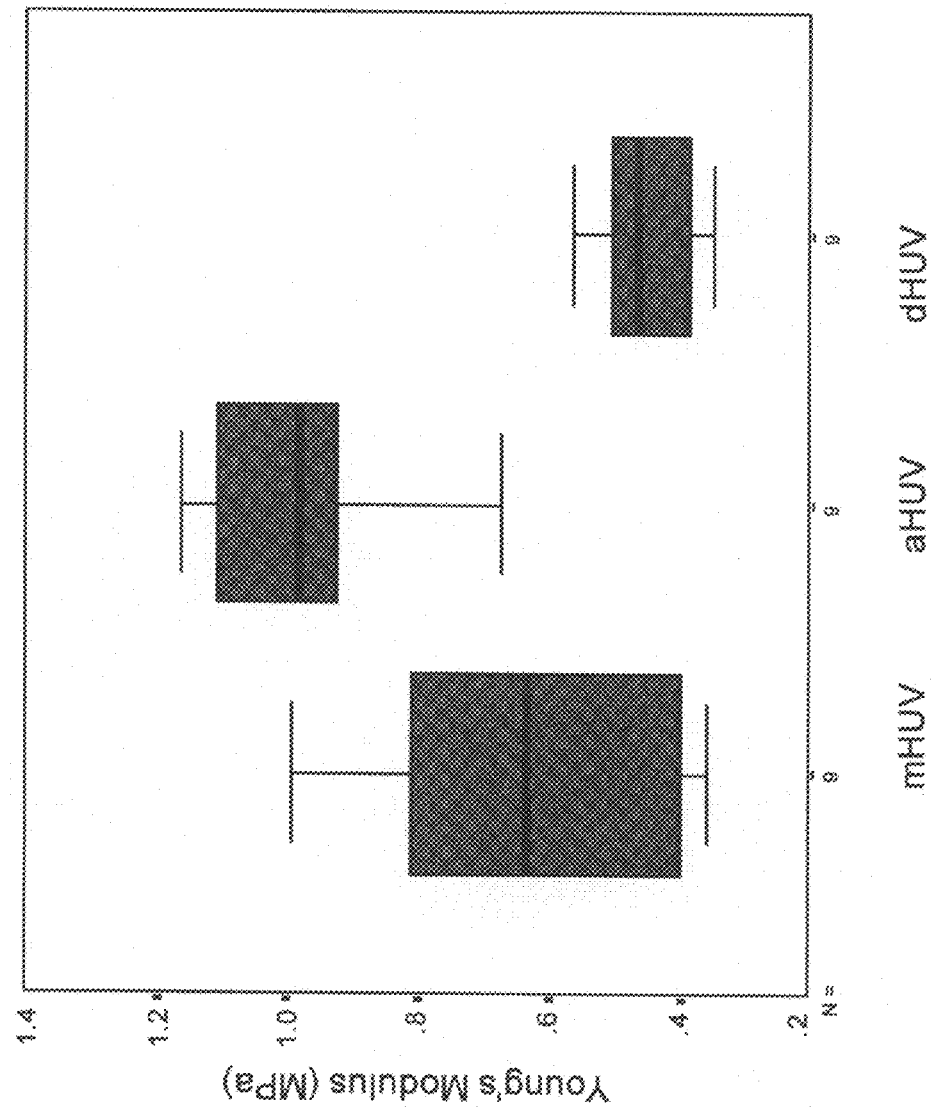
FIG. 9 graphically illustrates Young's Modulus for mHUV, aHUV, and dHUV. Young's Modulus, a measure of elasticity, is significantly higher with the Automated-Dissection Method.
Figure 10:
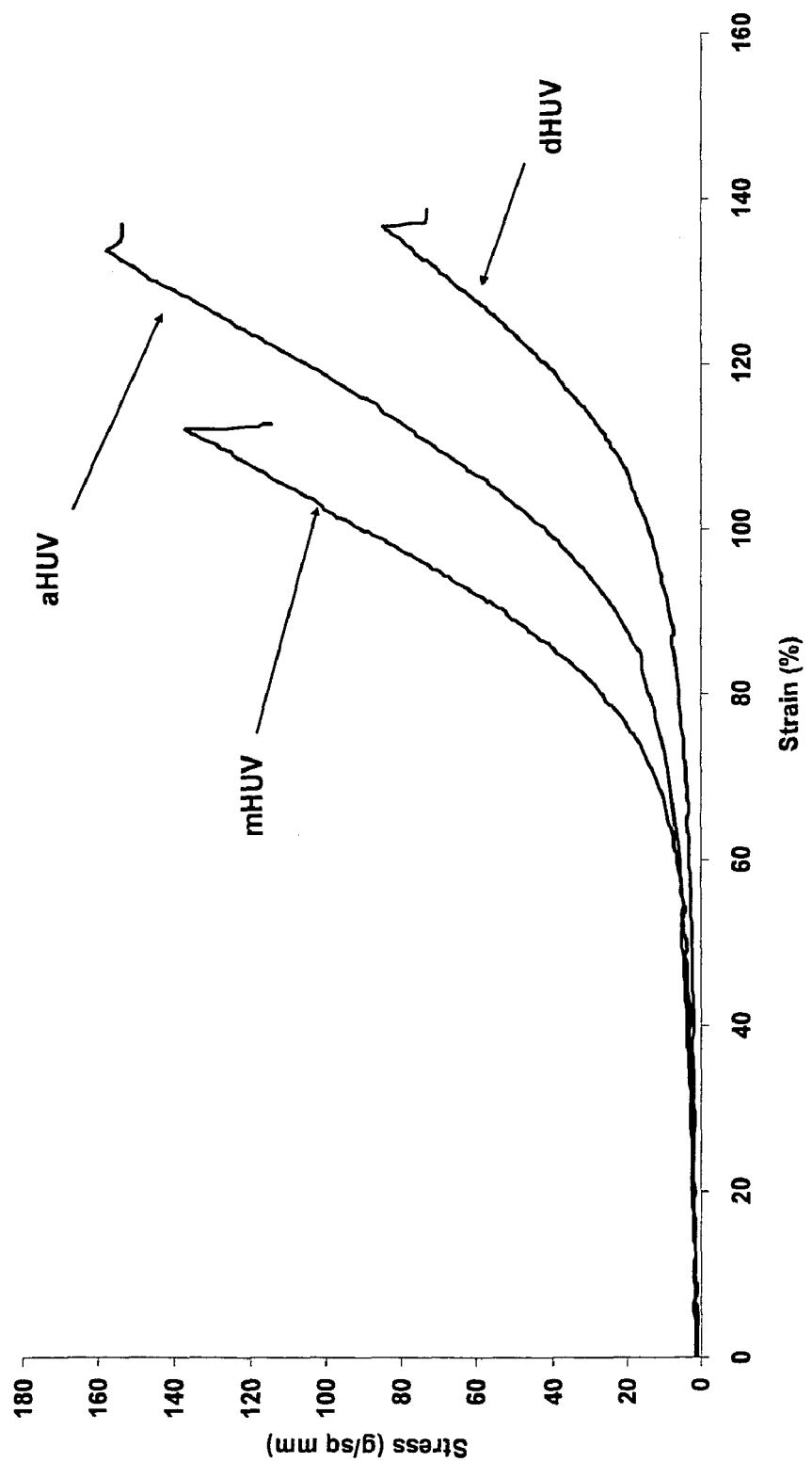
FIG. 10 graphically illustrates representative stress-strain graphs for mHUV, aHUV, and dHUV. A biphasic relationship also seen by in vivo soft tissues is observed.
Figure 11:
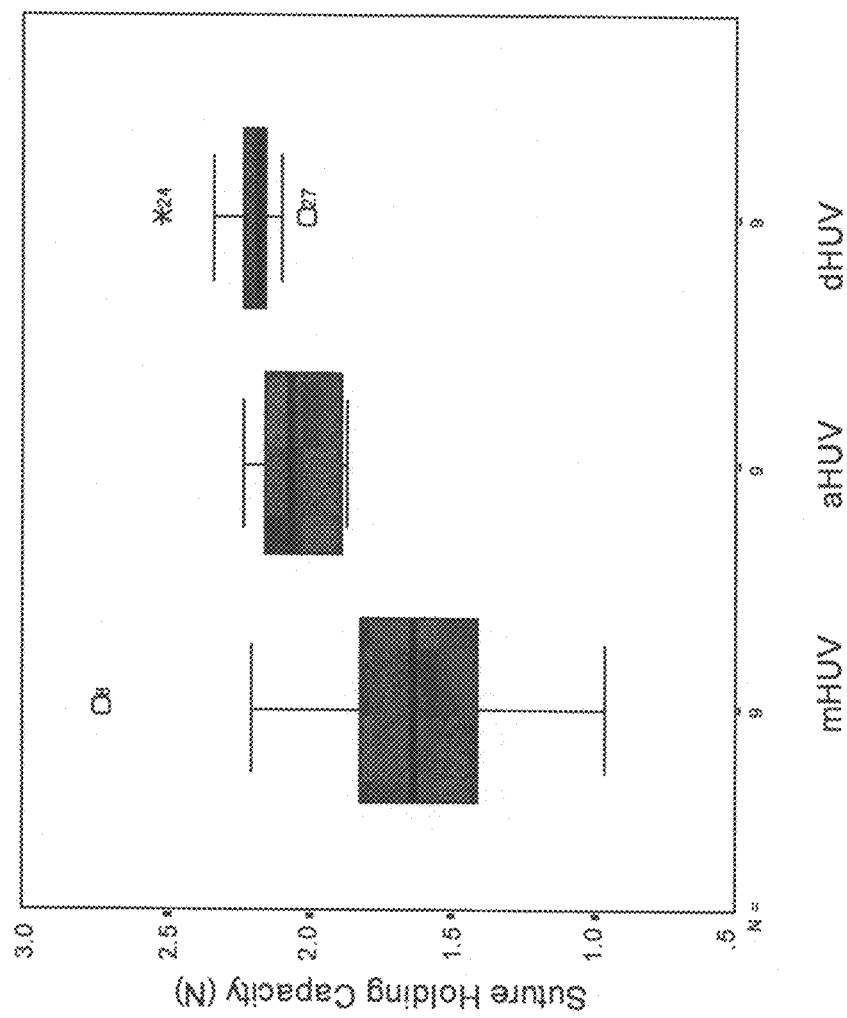
FIG. 11 illustrates suture holding capacity of mHUV, aHUV, and dHUV under a progressively applied force. While the differences between the two dissection methodologies are not significant, range and standard deviation are decreased with automated dissection.

In addition, the use of the automated dissection procedure also shows a significant reduction in sample-to-sample mechanical variation compared to manual dissection, as shown in FIG. 6. Table 1 provides an overview of the mechanical properties of the scaffold; the data on compliance values is also shown in FIG. 7, while the data on suture retention is shown in FIG. 11, and the data on Young's Modulus is shown in FIG. 9. FIG. 10 illustrates the relationship between applied stress (g/mm$^2$) and strain (elongation).

TABLE 1

|  | Compliance (%) | Suture Retention (g) | Young's Modulus (g/mm$^2$) |
|---|---|---|---|
| Manual Dissection (untreated) | 5.7 ± 2.1 | 171.78 ± 53.52 | 64.7 ± 24.4 |
| Auto Dissection (not decellularized) | 4.6 ± 1.2 | 207.45 ± 13.69 | 76.7 ± 17.9 |
| Auto Dissection (decellularized) | 5.7 ± 1.3 | 224.95 ± 15.01 | 45.9 ± 7.6 |

The relationship between vessel expansion and applied internal pressure for the tissue graft of the present invention was assessed (FIG. 7). No statistical difference in compliance values was found between the mHUV, aHUV, and the dHUV over a pressure range of 80-120 mmHg. Compliance (Δd/d) results for the mHUV, aHUV, and dHUV were 5.7±2.1, 4.6±1.2, and 5.7±1.3%, respectively. Similar to the burst pressure results described above in relation to FIG. 6, a significant reduction in sample variation is noted between manual and automated dissection procedures.

Figure 8:
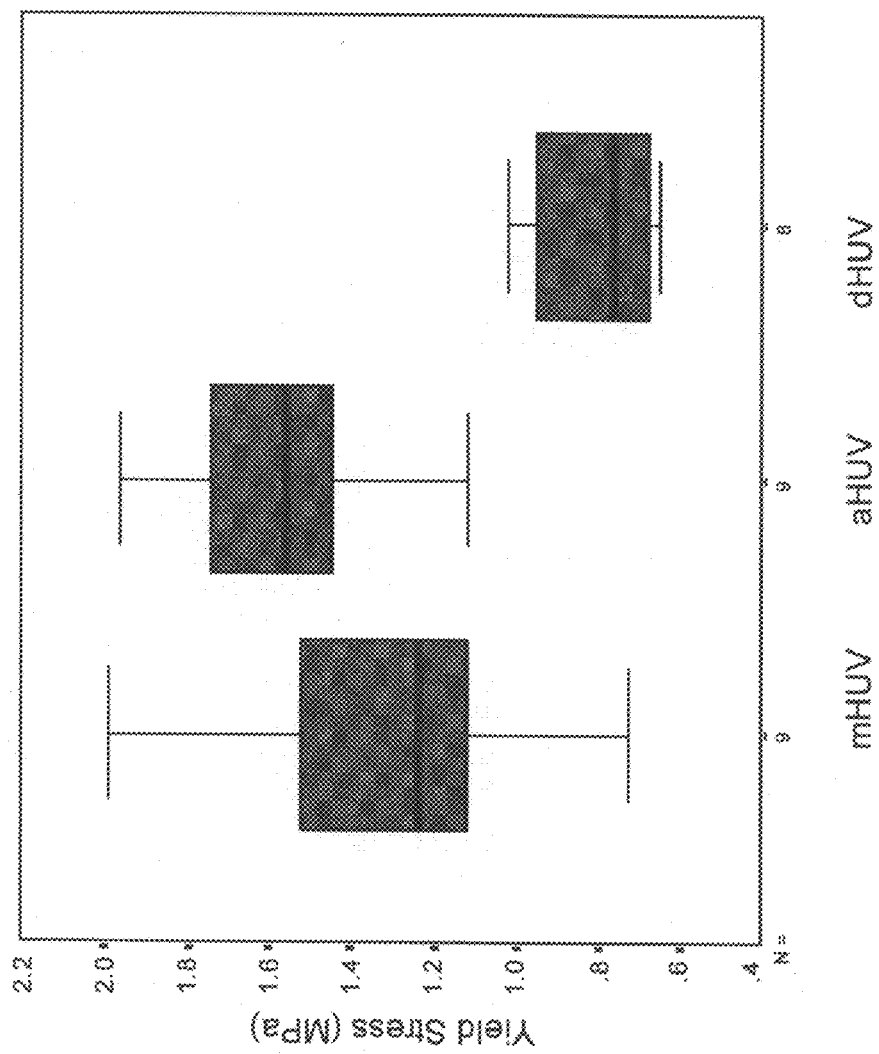
FIG. 8 graphically illustrates yield stress of mHUV, aHUV, and dHUV. No significant change in the yield stress was observed in dissection methodologies. There was a decrease with the chosen represenative decellularization method.

Data from stress strain analyses for mHUV, aHUV and dHUV were used to determine yield stress (FIG. 8) and Young's Modulus (FIG. 9). No significant difference was found in the yield stress between the mHUV and the aHUV samples, with yield values at 1.31±0.64 N/mm$^2$ and 1.56±0.76 N/mm$^2$ respectively. However a significant reduction was found with the dHUV samples, showing a reduced yield value of 0.81±0.45 N/mm$^2$ (FIG. 8).

Young's moduli of aHUV showed a significant decrease in elasticity over the mHUV sections, with values for the mHUV and the aHUV being 0.64±0.24 and 0.76±0.18 N/mm$^2$, respectively. The dHUV displayed a more elastic property, with a modulus value of 0.45±0.075 N/mm$^2$, that was not significantly different from the mHUV (FIG. 9). Representative stress-strain curves (FIG. 10) show a general increase in strain at the point of failure as the vessels are progressively treated. In all cases the vessels have retained the biphasic nature of natural blood vessels.

The suture holding capacity of each group (mHUV, aHUV, and dHUV) under a progressively applied force was also determined (FIG. 11). No significant difference was found between the aHUV (171.78±53.52) and the dHUV (207.45±13.69); however the mHUV had a lower suture holding capacity than the aHUV or the dHUV (224.95±15.01 g).

After the decellularization and washing processes, analysis of hematoxylin stained sections displayed no intact endogenous cell nuclei (see FIG. 12A, manually dissected control; and FIG. 12B, post automated dissection and decellularization); however some disruption to the ECM fibers was observed. Unlike the liquid $N_2$ treated samples, no gross fractures were noted for the aHUV when prepared at −80° C. on a tubular mandrel. hVSMC seeded to a final density of 3000 cells/mm$^2$ onto the ablumenal surface of the dHUV and cultured over a 7 day period demonstrated cellular attachment and migration into the acellular tissue, as shown in FIG. 12C.

Figure 13:
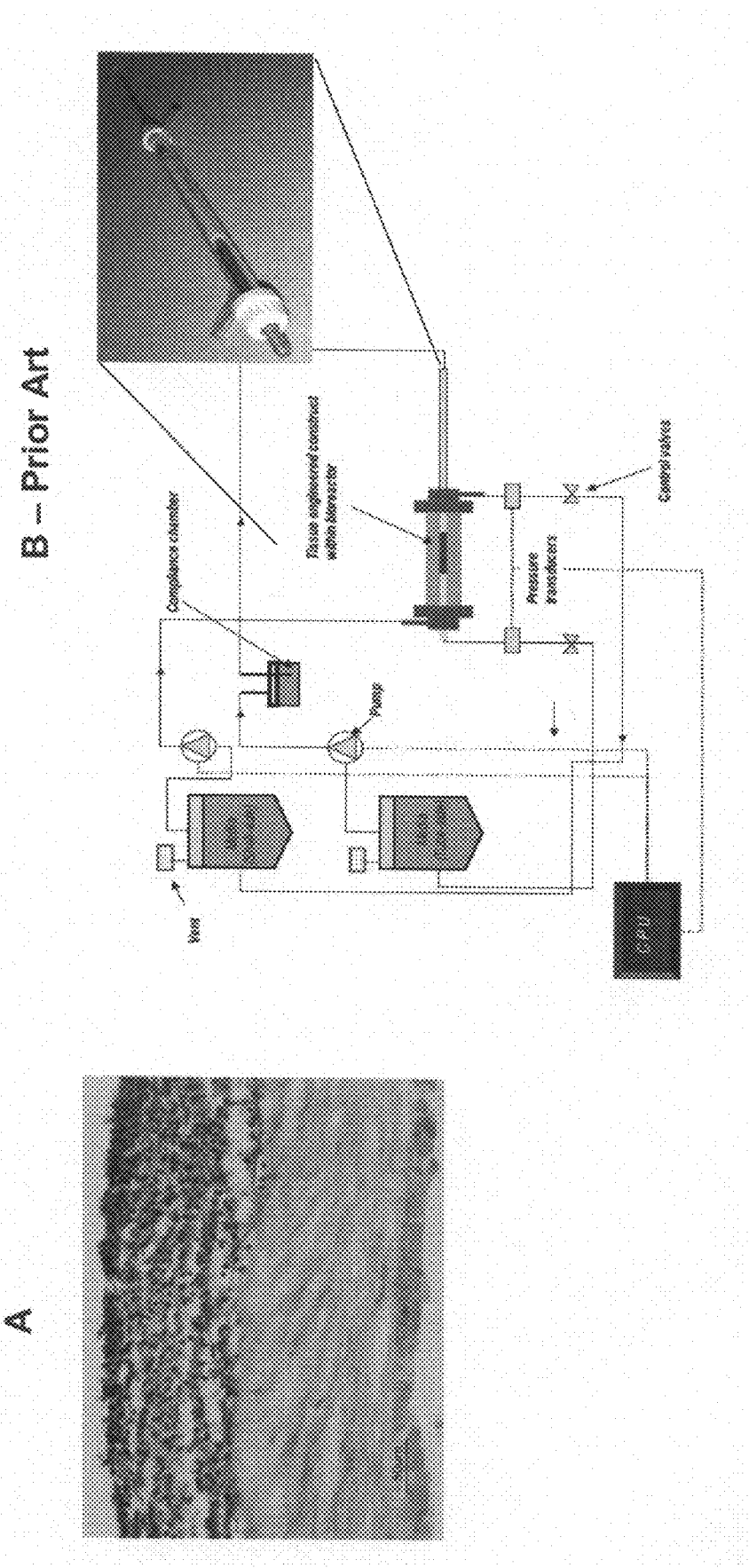
FIG. 13A contains photographs of H&E stained histological images of primary human smooth muscle cells seeded at $2.5 \times 10^3$ cell/mm$^2$ onto the dHUV matrix (cut to 400 µm) cultured for 5 days.
FIG. 13B is a diagrammatic representation of a single bioreactor and accompanying process flow circuits developed in previous studies of the inventor, and a photograph of the assembled bioreactor with mock graft enclosed.
Figure 15:
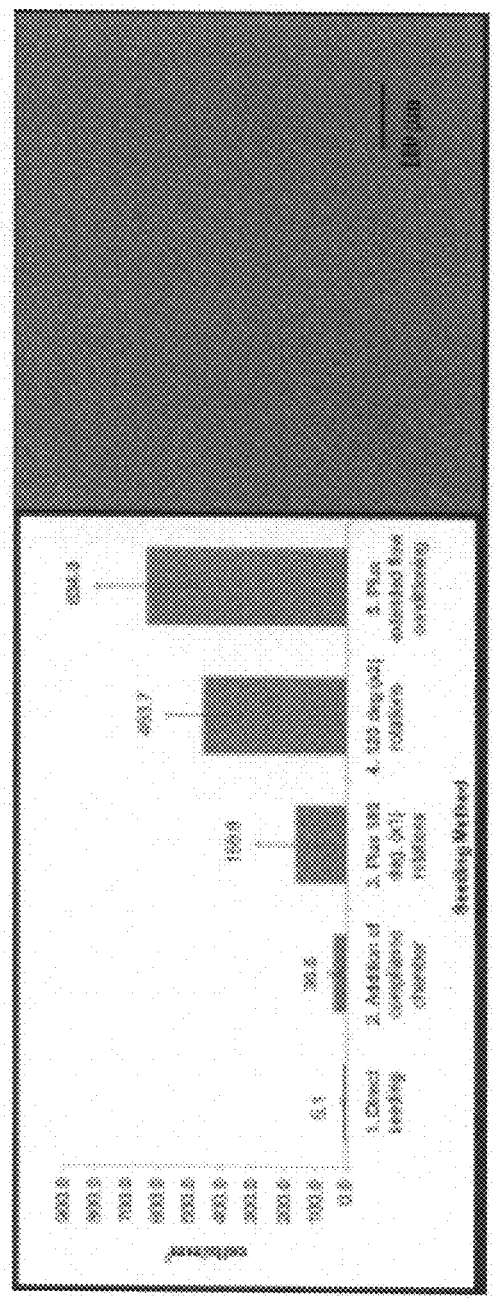
FIG. 15 contains photographs illustrating the development of a confluent mono-layer of EC cells on the porcine carotid arterial matrix under physiological flow conditions, with flow rates cumulating at 165 ml/min (1.33 Hz). Results show EC nuclei stained with DAPI adhered to the matrix after 10 days perfusion using seeding method 5 with extended flow conditioning, resulting in an adhered cell density of 643 cells/mm$^2$.

FIG. 13A also demonstrates that the decellularized scaffold supports several mammalian cell lineages, including but not limited to, primary human smooth muscle cells and fibroblasts, and that the cells adhere and proliferate over extended time frames, providing strong evidence for active remodeling. FIG. 13B is a schematic drawing of a prior art process flow that may be utilized in one method of the present invention. The process flow delivers variable gas and mechanical conditions to the HUV. The bioreactor is designed specifically to control the flow conditions entering and contacting the developing construct. For example, to enhance the fluid dynamics, a modified luminal inlet was designed to ensure that fully developed flow enters the reactor to better control the fluid shear to exposed endothelial cells. The fluid mechanics equation for 'entry port flow conditioning' was used to determine entry length:

$$L_{ent}/D=0.370 \exp(-0.148Re)+0.0550Re+0.260$$

where D=diameter, Re=Reynolds number (proportional to flow rate), and $L_{ent}$=the flow conditioning entry port length to ensure 99% fully developed flow into the reactor (Perry et al., 1998). It is this functional design that proved successful in maintaining vascular EC and VSMC up to 5 weeks with a luminal flow rate of 150 ml/min and shear rates up to 3100 s$^{-1}$, as shown in FIGS. 13 and 15.

Figure 14:
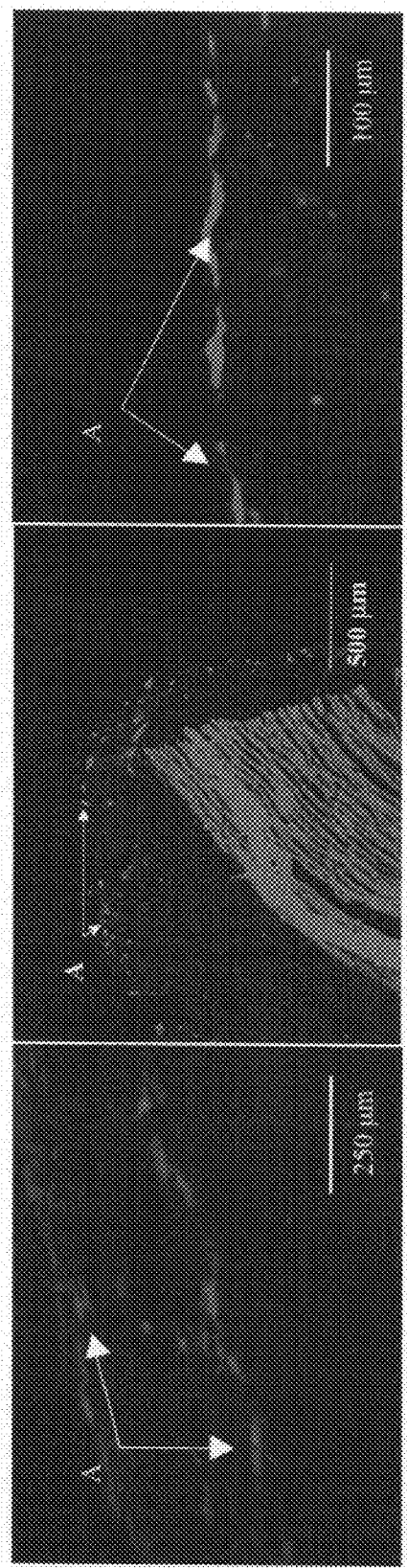
FIG. 14 contains prior art photographs of a porcine carotid arterial matrix that is stained for Cathepsin-L (left), MMP-2 (middle), and MMP-9 (right) after 3 weeks culture. The presence of cells corresponds with areas of immunolabeled enzyme (A) within the adventitial layer of the matrix.

Prior experiments using the porcine carotid artery have shown the utility of ex vivo tissue as a tissue engineering scaffold by illustrating improved tissue processing, mechanical properties, and culture of VSMC and EC with 3D perfusion systems (McFetridge et al., 2004; and McFetridge et al., 2004; both of which are hereby expressly incorporated herein by reference in their entirety). In these studies cells were cultured in vitro under mimicked hemodynamic conditions using the vascular bioreactor and perfusion system (as above). These experiments have shown that cell populations remained viable until cultures were terminated (35 days), expressing remodeling enzymes in a temporal fashion. Immuno-labeled matrix metalloprotease 2 and 9, and cathepsin-L were conjugated to either FITC or Rodamine fluorescent markers to localize remodeling activity, as shown in FIG. 14.

The above-described prior art experiments using a decellularized porcine carotid arterial matrix provide methodologies for assessing endothelial cell (EC) adhesion to the HUV of the present invention in concert with hVSMC. Methods are described herein to seed and adhere high densities of primary human VSMC and human umbilical vein endothelial cells (HUVEC) to the matrix of the present invention. EC cultured under conditions that mimic the in vivo hemodynamic environment (shear rates up to 3100 s−1, with flow rates of 165.5 ml/min at 1.33 Hz) are utilized in accordance with the present invention, and it has been shown herein that EC seeded on the carotid matrix remain adhered (and viable) under physiological flow, pressure, and shear to result in EC densities approaching that of a competent endothelium (FIG. 15) (McFetridge et al., 2004). VSMC seeding on the porcine arterial matrix have also shown cell dense layers on the matrix surface (FIG. 14).

This method of the present invention describes the development of a multi-functional ex vivo acellular bioscaffold derived from the human umbilical cord vein for the development of tissue engineered blood vessels. The tissue graft of the present invention has been shown to act as a 3D support for guided vascular tissue regeneration, demonstrating cellular infiltration into the HUV. Further, the present invention also demonstrates the utility of the HUV and bioreactor as an ideal experimental system to further the understanding of important biological events such as wound repair, phenotype modulation, and cell migration in a complex human tissue matrix where the in vivo wound environment is mimicked.

EXAMPLE 2

By progressively modifying cell culture conditions to mimic the environment an implanted construct might encounter in vivo, the effect of mechanical force and hypoxia on hVSMC proliferation, migration, and remodeling processes is assessed. In order to quantify these distinct environmental conditions, three areas are investigated: (1) traditional cell culture systems, (2) introduction of mechanical stress, and (3) exposure to hypoxic conditions. Variation between the three areas is quantified using standardized experimental and analytical methods.

First, the ability of the HUV bioscaffold to provide a favorable environment for early regenerative events is assessed. To quantify the regenerative capacity of the decellularized HUV bioscaffold under traditional 'static' tissue culture conditions using primary human SMC is investigated. Cell proliferation and viability using standard histological and immunohistochemical techniques is investigated. Image analysis software assessed hVSMC cell migration and remodeling from the seeded surface into the inner bioscaffold. Quantitative image analysis software provides measured cell migration within the tissue repair scaffold. The scaffold's remodeling capacity is assessed by evaluating elastin deposition and the expression patterns of matrix remodeling enzymes including MMP-1, 2, 8 and 9 and procollagen-1 expression. Samples are assessed for the presence of each enzyme/protein and to determine any temporal expression patterns that may occur. Cells are evaluated for expression of cell specific phenotypic markers α-actin and myosin heavy chain.

Figure 16:
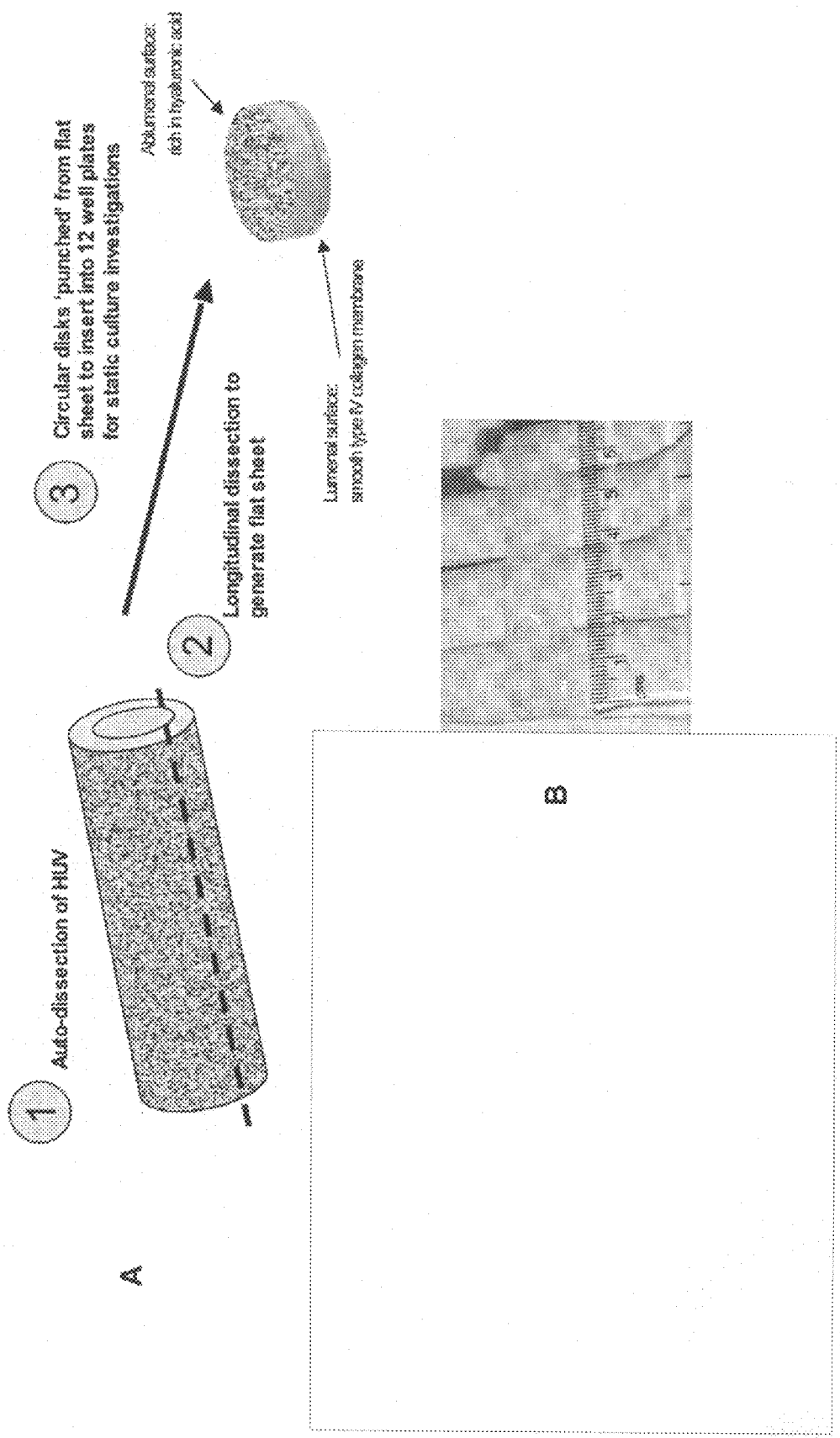
FIG. 16A is a schematic illustration of the dissected HUV before longitudinal dissection (1) to generate a flat sheet of tissue (2). Circular disks are 'punched' from the sheet (3). The upper surface (to be seeded) represents the hyaluronic acid rich abluminal surface with the lower surface being the Type IV collagen basement membrane of the vessel lumen.
FIG. 16B is a photgraph of a HUV of the present invention after longitudinal dissection to produce a flat, uniform scaffold ready for decellularization (and having a wall thickness of about 750 µm).

Flat sections of decellularized HUV (wall thickness of 750 μm), are cut using a circular hole punch (16 mm OD), see FIG. 16. Sections are sterilized and depyrogenated by using 0.1% peracetic acid (v/v) and 4% EtOH (v/v) in distilled $H_2O$, prepared in a solution ratio of 20:1 solvent (ml) to tissue weight (g) for 2 h (Hodde et al., 2002). HUV sections are then washed in PBS until the pH is stabilized at 7.2, then inserted in 12 well tissue culture plates where they are incubated in standard cell culture media for 2 hours prior to cell seeding.

To maintain consistency between static cultures and later bioreactor cultures, a collagen hydrogel is used as a cell delivery mechanism. hVSMC is expanded in culture (as described herein) and seeded at a density that approximates a layer of cells 2 deep (~1200 cell/mm$^2$). Cell density is based on an approximate cell dimension of 25×65 μm (1625 μm$^2$), a total of 6.1×10$^5$ cells/scaffold. Hydrogels are made on ice to a final concentration of 1.25 mg/ml collagen with a cell density 8.1×10$^5$ cell/ml. Each 16 mm HUV scaffold disk is seeded with 1 ml of the cell/hydrogel solution. Triplicate samples for each time point are cultured at 37° C., 5% $CO_2$ and assessed at days 1, 5, 10, 20, and 30. The regenerative capacity of the HUV bioscaffold is quantified by assessing proliferation and viability, migration, and remodeling activity, as well as mechanical properties.

The effects of mechanical stimuli on hVSMC behaviour and metabolism within the HUV bioscaffold are also examined. Limiting factors such as the mass transfer of nutrients, gasses, and wastes can be improved through the use of uniform convective flow. Convective flow is delivered by applying a cyclic pressure gradient to improve mass transfer to enhance the regenerative capacity of seeded scaffolds by providing an enriched milieu capable of attaining and maintaining higher cell densities. In addition, the mechanical environment induces differential gene expression. Gene expression in the vascular system, like other organs in the body, is influenced strongly by the mechanical environment, and has been shown to be an important factor in maintaining in vivo-like cellular phenotype (Seliktar et al., 2001; Seliktar et al., 2000; Kim et al., 1999; and Kim et al., 2000). Mechanical forces within blood vessels are complex, with mean shear rates ranging between 10 and 4000 s$^{-1}$ for vessels with lumens of 3-6 mm. To mimic these forces, the bioreactor and dual circuit process flow is used. The HUV bioscaffold remains in tubular form within the bioreactor, allowing force (pressure) to be applied to the luminal surface. This transmits mechanical shear not only to the luminal surface, but throughout the scaffold wall in a cyclic fashion that emulates the vasculature. Media is perfused through the luminal flow circuit at a standardized flow rate of 75 ml/min generating a shear rate of 100 s$^{-1}$ at the luminal surface. Using a peristaltic pump and the control valve down-stream of the bioreactors (see FIG. 13B), pressure within the luminal flow circuit is increased to a mean pressure of 100 mmHg with an exerted cyclic mechanical force of 0.0133 MPa. Increased pressure increases force per unit/area, causing the scaffold to increase in diameter, thus inducing mechanical shear on cells embedded within the scaffold. The hydrogel seeding method creates a uniform layer of cells on the scaffold surface. Three independent bioreactors and process flow circuits are used to obtain triplicate samples at days 1, 5, 10, 20, and 30 to quantify the regenerative capacity of the HUV bioscaffold. Cross-linked and non-cross-linked acellular scaffolds are assessed to determine the importance of restricted migration as a result of cross-linking.

The combined effects of controlled mechanical stimuli and hypoxia on hVSMC behaviour and metabolism within the HUV bioscaffold are also determined. Clearly the medial and outer layer of the construct are exposed to reduced $O_2$ tensions compared to the $O_2$ rich lumen. However, traditional culture conditions have elevated $O_2$ levels and therefore are grossly dissimilar to in vivo conditions. Under these stressed conditions, the abluminal surface will be hypoxic with elevated $CO_2$ concentrations, reduced nutrient availability and increased levels of metabolic wastes due to the lack of a functional vasculature within the vessel wall. Conversely, the luminal surface is highly oxygenated with improved gas exchange (normoxic).

Figure 17:
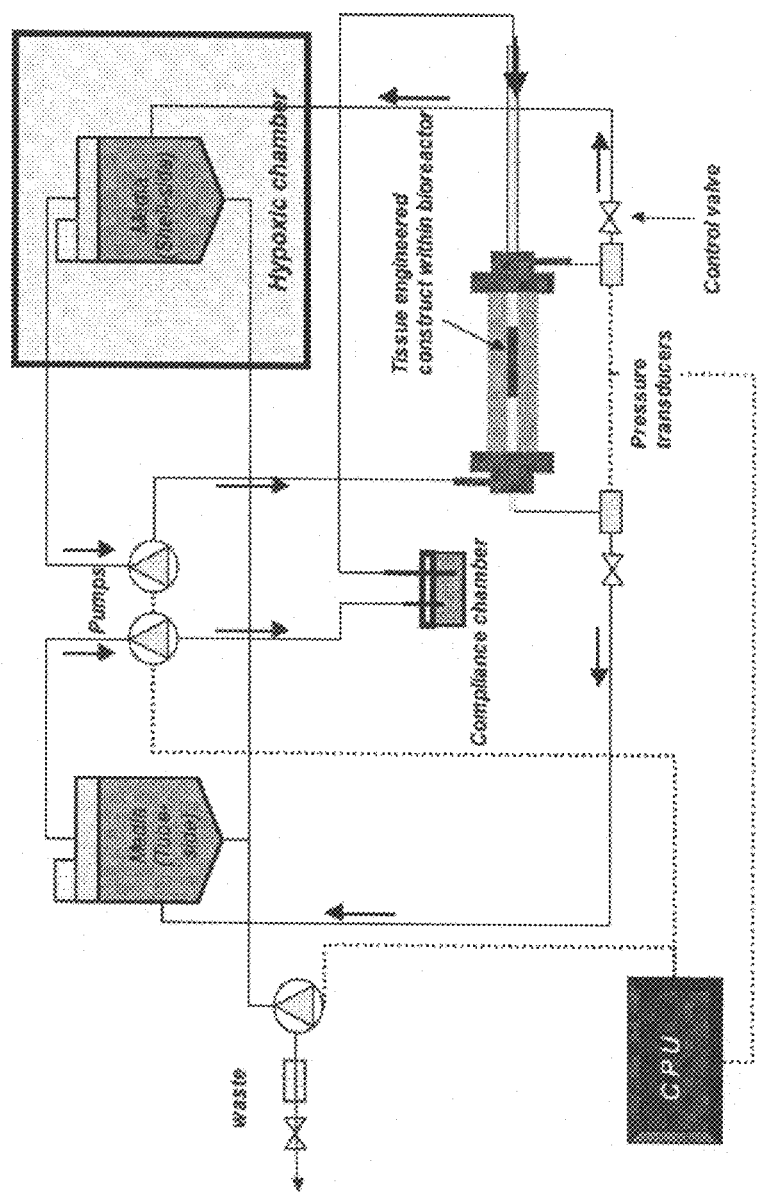
FIG. 17 graphically illustrates an overview of a process flow with a single perfusion bioreactor for utilization in the methods of cell seeding a decellularized matrix of the present invention. Using a controlled gasses incubator, hypoxic conditions with a PaO$_2$ of 20 mmHg is achieved (~40 mmHg minimum for normal healing).

In wound healing, hypoxia can be defined as an insufficient supply of oxygen to allow the healing process to proceed at a normal rate. Hypoxic conditions within the wound can vary substantially, in spatial and temporal concentrations of $O_2$. Conditions may support basal tissue maintenance at one time, but not enough to allow for growth or healing at another. As such, defining 'hypoxia' as an absolute value for $PO_2$ is difficult. In anesthesia, hypoxia is defined as an oxygen saturation less than a $PaO_2$ of <60 mmHg or <90% (Feeley, 1994). This is clearly higher than the tissue oxygen pressure of 40 mmHg needed to, for example, reliably heal a leg wound (Mathieu et al., 1990; and Bouachour et al., 1996). Clearly gas tensions are important regulators of wound healing, and as a direct comparison (ambient $O_2$ and $CO_2$ 5.0%), the influence of a hypoxic environment on the regenerative capacity of hVSMC within the HUV bioscaffold is assessed. The $O_2$ tension is modulated, and the regenerative capacity of the HUV scaffold is quantified by assessing hVSMC proliferation, migration, mechanical properties, and remodeling activity. Traditional tissue culture gas environments are set to ambient $O_2$ ($PaO_2$ of ≈100-120 mmHg) and $CO_2$ of 5.0% to maintain the pH. The use of a perfusion bioreactor further increases the $PaO_2$ due to the recirculating media; under these conditions, the oxygen levels can reach as high as $PaO_2$ 180 mmHg (McFetridge, 2002). In this investigation, $CO_2$ levels will remain at 5.0%, but the $PaO_2$ is reduced below the $PaO_2$ threshold of 40 mmHg to 20 mmHg. By taking advantage of the bioreactor design where the two surfaces are separated and provided with separate media sources, the gas environment is independently controlled such that each surface of the scaffold is exposed to a defined gas composition (in this case, a $PaO_2$ of 20 mmHg and 5% $CO_2$). To achieve this, the media containment vessels that supply the bioreactors shell-side (the abluminal seeded surface) are fitted with atmospheric gas-exchange filters to allow the media to equilibrate with the surrounding gas environment. Using gas-impermeable tubing, these vessels are contained in a controlled gasses environment (MACS VA-500) at 37° C. with a $PaO_2$ of 20 mmHg. The remaining components of the process flow are maintained in a second, large capacity incubator (Sheldon Mod., 1927) under standard conditions of ambient $O_2$, 5% $CO_2$ at 37° C. (FIG. 17). From a method perspective, the only difference between mechanical stress and hypoxic conditions is control of the gas tension. hVSMC are seeded onto the outer surface of the HUV bioscaffold to create a uniform layer of cells on the scaffold surface. Three independent bioreactors and process flow circuits are used to obtain triplicate samples at days 1, 5, 10, 20, and 30. Both cross-linked and non-cross-linked acellular scaffolds are assessed to determine cellular interactions and the significance of reduced $O_2$ tensions. The regenerative capacity of the HUV bioscaffold is quantified under hypoxic conditions by assessing the same parameters of hVSMC cell proliferation, migration, and remodeling activity, etc.

EXAMPLE 3

In another embodiment of the present invention, the tissue graft of the present invention is utilized for the development of a multi-functional ex vivo acellular bioscaffold for oral wound repair. Due to structural and morphological variation between the upper (lumen) and lower (ablumen) surfaces of the vascular scaffold, the smooth, type IV collagen surface is disposed outermost, in contact with the oral cavity, and the more fibrous surface of type I collagen and hyaluronic acid is disposed directly on top of the wound site. These investigations examine the rate of cell re-population and remodeling of the scaffold from cells directly within the wound site. The second application of the present invention in oral wound repair is as a tissue engineered construct seeded with autologous cells, then implanted as functional tissue. The experiments described herein support both applications by gaining a thorough understanding of the material's ability to re-integrate with biological systems, and secondly to quantify the performance under simulated conditions of mechanical strain and hypoxic conditions.

By cutting the umbilical vessel longitudinally to create a mechanically robust, flat sheet (15-20 mm wide×>100 mm long), this material is designed to rebuild excised regions of oral tissue after treatment of periodontitis or other oral reconstructive surgeries. The unique functionality of this bioscaffold can be attributed, in part, to its multilayered composite structure, where unique properties are utilized to promote wound repair. For example, the type IV collagen basement membrane that lines the luminal surface of the tissue graft has been shown to be resistant to microorganism penetration. Further, the abluminal surface of the tissue graft allows fibroblast migration, indicating active ECM remodeling. In order to fully integrate and guide tissue repair, cells from either the wound-site or from a seeded autologous source, need to interact in a positive fashion with the implanted bioscaffold.

By progressively modifying cell culture conditions to mimic the wound environment, the effect of mechanical force and hypoxia on primary human gingival fibroblasts (pHGF) proliferation, migration, and remodeling of the HUV into neo-tissue is assessed in the same manner as described in Example 2, except as described in detail herein below. These analyses further prove a valuable tool to a better understanding of the wound healing environment. To quantify each of the effects of environmental conditions, three areas were studied: (1) traditional cell culture systems, (2) modulation of the mechanical environment, and (3) exposure to hypoxic conditions. In order to separate the mechanical, as well as the gas tension environments, between the wound-site/scaffold interface and the oral cavity/scaffold interface, the bioreactor and dual circuit process flow was used to deliver mechanical stimulation and oxygen tensions.

The bioreactor-based perfusion system to mimic aspects of the wound environment to determine responses of seeded pHGF was assessed. By understanding the effects of mechanical stimulation and hypoxia on tissue regeneration it is possible to determine parameters that induce active tissue regeneration.

The ability of the HUV bioscaffold to provide a favorable environment for early wound healing by human gingival fibroblasts (pHGF) under traditional 'static' growth conditions is determined. Cell migration and remodeling activity are fundamentally important in wound healing processes. Experiments are conducted as described in Example 2, except that primary human gingival fibroblasts (pHGF) are utilized, scaffold/cell constructs are evaluated for cell density, viability, proliferation, and the expression of cell specific phenotypic markers, and the expression patterns of matrix remodeling enzymes MMP-2, 13 and procollagen-1 expression are evaluated.

Regarding cell proliferation and viability, the ability of pHGF to proliferate and be maintained on the HUV scaffold is investigated. Cell proliferation is assessed using the PicoGreen dsDNA quantification assay, with cell viability being confirmed using BrU incorporation into RNA (to determine active RNA transcription).

Cell migration and remodeling activity are fundamentally important in the wound healing processes. Cell migration is quantified using image analysis software. The remodelling capacity is assessed by monitoring the expression of key remodeling enzymes using immunohistochemical analysis of pro-collagen-1 and matrix metalloproteases 2 and 13.

The ability of cells to remodel the ECM relies on fundamental processes of degradation and expression of ECM components. This process, if not complete, has the potential to result in a loss of mechanical integrity. The material's suture holding capacity, yield stress and strain, modulus, as well as the material's ultimate failure over time, is assessed. These assays further the understanding of this material's remodeling capacity and the cellular effects of ECM stability.

The effects of mechanical stimuli on gingival fibroblast behavior and metabolism within the HUV bioscaffold (3D dynamic) are examined as described in Example 2, with the exception that the convective flow applies a cyclic, pulsed pressure gradient that improves mass transfer and delivers a controlled mechanical stimuli to the construct.

Mechanical forces within the oral cavity are complex, with shear rates ranging between 10 and 1000 $s^{-1}$ which are complicated by salivary output, mastication, speech etc. (Shama et al., 1973). In order to mimic these forces, the bioreactor and dual circuit process flow is used as described in Example 2, except as described herein below. Using a peristaltic pump and the control valve down-stream of the bioreactors (see FIG. 13B) pressure within the luminal flow circuit is cyclic with a peak pressure of 50 mmHg that exerts a cyclic mechanical force from 0 to a peak of 0.068 MPa. Using the collagen hydrogel seeding method, hydrogel/cell constructs contract off the bioreactor inner wall and onto the abluminal surface to create a uniform layer of cells on the scaffold surface. The regenerative capacity of the HUV bioscaffold is quantified by assessing proliferation, migration, mechanical properties, and remodeling activity of pHGF cells. Cross-linked and non-cross-linked scaffolds are assessed to determine the importance of inhibited cell migration.

The combined effects of controlled mechanical stimuli and hypoxia on gingival fibroblast behavior and metabolism is determined within the HUV bioscaffold as described herein above. When used clinically to cover/protect an oral wound, it is certain that the two surfaces of the scaffold will be exposed to two very different oxygen environments. The wound-site/scaffold interface will likely have reduced $O_2$ (hypoxic) and increased $CO_2$ concentrations due to the lack of functional vasculature, reduced nutrient availability and increase levels of metabolic wastes. Conversely the oral cavity/scaffold interface will be highly oxygenated with improved gas exchange (normoxic).

Primary human gingival fibroblasts (pHGF) are seeded onto the outer surface of the HUV bioscaffold to create a uniform layer of cells on the scaffold surface as described in Example 2. The regenerative capacity of the HUV bioscaffold under hypoxic conditions is quantified by assessing pHGF proliferation, cell migration and remodeling, as well as assessing the change in mechanical properties over time.

One of the primary functions of the HUV matrix is to protect the wound from the normal bacterial flora of the mouth, and it appears that this tissue biomatrix prevents microbial invasion through the biomatrix. Therefore, bacterial attachment and biofilm formation on the HUV biomatrix are evaluated using a static biofilm assay. These studies use three bacterial species including *Staphylococcus aureus*, *Pseudomonas aeruginosa*, and *Actinobacillus actinomycetemcomitans*. These bacterial species were chosen for several reasons: *S. aureus* is a model organism for studying biofilm formation by gram positive bacteria and is a common contaminant of surgical implants; *P. aeruginosa* is the model bacterium for studying attachment and biofilm formation in gram negative bacteria; *A. actinomycetemcomitans* is a common inhabitant of the human oral cavity and has been shown to be associated with periodontal disease. Further, strains of each of these bacteria are available which express the green fluorescent protein (GFP). Adhesion is assessed by examining attachment of each of these GFP labeled strains to sections of the tissue biomatrix. Attached bacteria is visualized using scanning confocal laser microscopy and quantified by standard plate counting of homogenized tissue samples. The goal of these studies is to evaluate the ability of these bacterial species to form stable associations with the tissue biomatrix. These studies provide the necessary information to design focused experiments to evaluate attachment and biofilm formation under flow conditions using the existing dual circuit perfusion bioreactors and process flow system.

The above-described experiments serve as a base-line for future investigations that will further the understanding of the shear tolerance of adhered microbial populations on this human Type IV basement membrane.

Materials and Methods

Preparation and dissection of the human umbilical vein: Fresh human umbilical cords were harvested from full-term human placentas collected from the Delivery Suite at the Norman Regional Hospital, Norman, Okla. Cords were stored within 10 minutes of delivery at 5° C., and no more than 24 h until preparation for experimental use. Prior to dissection the cords were cleaned, and rinsed to remove residual blood. Cords were then cut to an initial length of 80 mm (10 mm was discarded from each end was discarded where clamping had damaged the tissue, final sample length for testing was 60 mm).

Manual dissection: A 200 mm long×6 mm outside diameter (OD) glass mandrel was inserted through the vein's lumen to guide the manual dissection process, see (FIG. 1A). Using a standard scalpel and forceps the arteries and mucous connective tissue that surround the vein were progressively excised (as uniformly as possibly), until a thickness of 750 µm±100 µm was achieved. These samples were designated 'manually dissected human umbilical vein' (mHUV) (FIG. 1B).

Automated dissection: A number of different methodologies were assessed to optimize the automated dissection process, including: cutting temperatures of −20° C., −80° C., and −196° C. and mandrel specifications of solid 316 stainless steel rod (6 mm OD×18 cm L), and 316 stainless steel tube (4 mm ID, 6 mm OD×18 cm L), to achieve an optimal dissection. In a similar fashion to the manual dissection method, the automated method required a stainless steel mandrel (6 mm OD) to be inserted through the vein lumen to straighten the vessel and retain its tubular shape during the excision procedure. The cord was then tensioned longitudinally and the spiraling structure of the vein 'unwound' to improve uniformity. The mounted cord was then secured at each end using 4 mm nylon zip-ties to minimize torque induced slippage during dissection. The accuracy of the procedure relied on the vein being in close, 'uniform' contact with the mandrel, to minimize raised or buckled sections that would otherwise result in variation in scaffold wall thickness, (FIG. 2A). All sections were progressively frozen within a sealed Styrofoam container at a rate of 2.5° C./min (Oegema et al., 2000). Vessels frozen to −20° C. and −80° C. were maintained at their terminal temperature for a minimum of 12 hours to ensure a uniform temperature throughout the vessel wall. Freezing vessels to −196° C. required progressive freezing to −80° C. (as above) then plunging samples into liquid nitrogen.

Mounted, frozen vessels were removed from frozen storage immediately prior to inserting the cord/mandrel into the lathe (Central Machinery, Mod 33647, China). Once the mandrel/cord was secured in the lathe, the rotational speed was set to 2900 rpm and then engaged. Using a high-speed steel cutting tool, designed for cutting soft materials, the cutting depth was set to 750 µm, the automatic drive was engaged at a rate of 5 mm/sec, until the cutting tool had transversed the cord section (FIGS. 2B-D). Automatically dissected HUV (aHUV) sections were then stored at −20° C. until required (minimum 4 hours). The time frame from removal from the −80° C. freezer to the completion of dissection and storage was <2.5 minutes. Sections were thawed by immersion in double-distilled water at 5° C. within a 5° C. refrigerator for 1 hour (Oegema et al., 2000; Bujan et al., 2000; and Pegg et al., 1997).

ecellularization: A representative decellularization process was used to determine the effect of processing on the HUV's mechanical properties. Due to the poor results of the −20° C. and −196° C. prepared segments, only vessels prepared at −80° C. were decellularized. Glass rods (3 mm OD) were inserted into the lumen of the vessel to aid diffusion prior to decellularization process. Each 80 mm long aHUV segment was immersed in a 25 ml solution of 1% (w/v) sodium dodecyl sulfate (SDS) for 12 hours, then rinsed (×3) in phosphate buffered saline (PBS). Sections were then washed for 12 hours in 25 ml of 75% (v/v) ethanol to remove the amphiphilic surfactant molecule and aid lipid extraction (McFetridge et al., 2004). Sections were then washed (×3) in 25 ml of PBS for one hour prior to use. These samples were designated decellularized human umbilical veins (dHUV).

Mechanical analysis: Samples were categorized into three groups: mHUV, aHUV, and dHUV. Each group was composed of nine samples: three separate cords with three data points obtained from each cord (n=9). To eliminate end effects, an additional 1 cm was removed from each end of each sample prior to mechanical analysis, leaving a total length of 6 cm (Hiles et al., 1995).

Burst Pressure and Compliance: Burst pressure and compliance were measured by progressive inflation of the vessel until rupture, whilst simultaneously recording the change in vessel diameter. The ends of each vessel section (6 cm), were attached to stainless steel adapters (4 mm ID/6 mm OD×6 cm L), and connected into a circuit of heavy walled silicone tubing (4.76 mm ID/7.94 mm OD). A modified syringe pump was then attached to one end of the tubing, with a pressure transducer (Master Test Type 220-4s, Mash Instrument Company, Skokie, Ill.) attached to the distal end (past the vessel) to monitor the change in internal pressure. The syringe pump injected double distilled water into the circuit at a rate of 5 ml/min until vessel rupture. Vessel diameter and pressure were recorded over time using a SVHS video recording system. Analog data was then converted to digital format and analyzed using MetaVue™ software (Universal Imaging Corp., Version 5.0r1, Downingtown, Pa.).

Compliance is defined as $$\left(\frac{\Delta d}{d\Delta P}\right)$$

(Hiles et al., 1995; and Roeder et al., 1999). Due to the dynamic nature of blood vessel mechanics, where the compliance value is dependent on the pressure range, the change in diameter ($\Delta d/d$) was assessed over a physiological pressure range (80 to 120 mmHg) (Roeder et al., 1999). At the point of vessel rupture the final pressure was recorded to determine the burst pressure for the vessel.

Stress-Strain Testing: A uniaxial tensile testing rig (United Testing Systems, Inc., Model SSTM-2K, Flint, Mich.) was used for all stress-strain analyses to determine the stress-strain relationship, Young's modulus, and yield stress. Circular vein samples were cut to 5 mm wide ringlets and loaded onto the machine using stainless steel L-hooks (McFetridge et al., 2004; and Hiles et al., 1995). Samples were preloaded to a stress of 0.5 g at a rate of 5 mm/min (McFetridge et al., 2004; and Courtman et al., 1995). Using the same extension rate 5 mm/min samples were stressed until failure (McFetridge et al., 2004).

Suture Holding Capacity: Suture holding capacity was assessed by applying uniaxial stress to the sutured samples (United Testing Systems, Inc., Model SSTM-2K, Flint, Mich.). Vein sections were cut longitudinally to form a 15 mm wide×80 mm long sheet. A single sterile 3-0 braided silk suture (Henry Schein, Melville, N.Y.) was passed through one end of the tissue section 2 mm below the cut edge, the other attached to the test rig (Billiar et al., 2001). Samples were preloaded to 0.5 g stress (5 mm/min). Data was then recorded at an extension rate of 125 mm/min until tissue failure (Billiar et al., 2001).

SEM analysis: Samples of the lumenal and the ablumenal surfaces of the aHUV were gently washed with phosphate buffere saline (PBS) (Gibco Life Technologies, Grand Island, N.Y.) three times for 5 minutes each, then fixed in 1% (v/v) glutaraldehyde (Sigma, St. Louis, Mo.) for 4 hours. Samples were then washed in PBS (3x) for 5 minutes each. This was followed by a treatment of 1% osmium in PBS for 2 hours. The samples were washed and dehydrated in graded ethanol (30%, 50%, 70%, 90%, 95%, and 100%, v/v) for 10 minutes each. Critical point drying was commenced in carbon dioxide (Autosamdri-814, Tousimis, Rockville, Md.). Samples were then gold sputtered (Hummer IV) and analyzed using a JEOL LSM-880 SEM.

Primary human cell isolation and culture: Mixed populations of primary human fibroblasts and vascular smooth muscle cells (hVSMC) were isolated as previously described by the explant method from human umbilical arteries (Kadner et al., 2004) and maintained with Dulbecco's Modified Eagle's Medium containing sodium pyruvate, L-glutamine, 100 U/ml penicillin and 100 μg/ml streptomycin (Gibco Life Technologies, Grand Island, N.Y.), and 10% fetal calf serum (Atlanta Biologicals, Norcross, Ga.). All cells were maintained at 37° C. in a 5% $CO_2$ environment and used between passages 3-5.

Cell Attachment Studies:

Fibroblast and smooth muscle cell seeding on the ablumenal surface: Mixed populations of primary human (neonatal) fibroblasts and smooth muscle cells (HVSMC) were seeded onto ablumenal surface of the decellularized human umbilical vein (dHUV) using a collagen hydrogel seeding method. Briefly, bovine collagen gels (Cell prime 100, Cohesion, Calif.) were made up to a concentration of 1.5 mg/ml and inoculated with $1 \times 10^6$ of the fibroblast/HVSMC mixed cell population. The solution was inoculated into ablumenal void of the vascular bioreactor and allowed to polymerize at 37° C. for 1 hour. After three days culture, gels contracted off the inner wall of the glass bioreactor onto the scaffold to a final cell density of approximately 3000 cells/mm$^2$. Vascular bioreactors consisted of glass cylinders with ports on each end for lumenal flow and two ports on the shell side for ablumenal flow. Flow of media was performed in a two circuit (lumenal and ablumenal) process flow system. Lumenal flow was maintained at 10 ml/min during gel polymerization (1 hour), and then progressively increased by 25 ml/min (each 6 hours) until a flow rate of 110 ml/min. was achieved. Cultures were maintained for total of 7 days at 37° C., 5% $CO_2$.

Histology and microscopy: HUV samples prepared for sectioning were fixed in 2% formal saline prior to paraffin embedding and sectioning. Samples seeded with hVSMC on the ablumenal surface were stained with hemotoxylin (Richard-Allan Scientific, Kalamazoo, Mich.) using standard protocols and sectioned to assess cell migration into the scaffold.

Statistics: Data sets were calculated from at least three independent experiments, each in triplicate (n=9), unless otherwise stated. Statistical significance was determined using analysis of variance (ANOVA) with Tukey HSD test. Significance was set at p<0.05.

HUV Cross-linking. Cross-linking is carried out according to the method of Mechanic et al (1992) (Mechanic, 1992; and McFetridge, 2002). Briefly, tissue is incubated for 24 h in a 0.5 M sucrose solution buffered in PBS at pH 7.4 followed by a two step cross-linking process. Tissue sections are incubated in the cross-linking solution (0.1% w/v methylene green in 4 M NaCl, buffered with 100 mM NaPO$_4$ at pH 7.4) for 24 hours at room temperature. Samples are maintained in the dark during this step. The second step (directed cross-linking) uses fresh cross-linking solution, with the reaction being driven by a 300 W halogen light source, suspended 15 cm above the surface of the reaction solution for 22 h maintained at 0±0.5° C. with 10 mL/min air sparged through the stirred reaction solution. Following cross-linking, scaffolds are washed in 1 L volumes of sterile distilled water.

Figure 18:
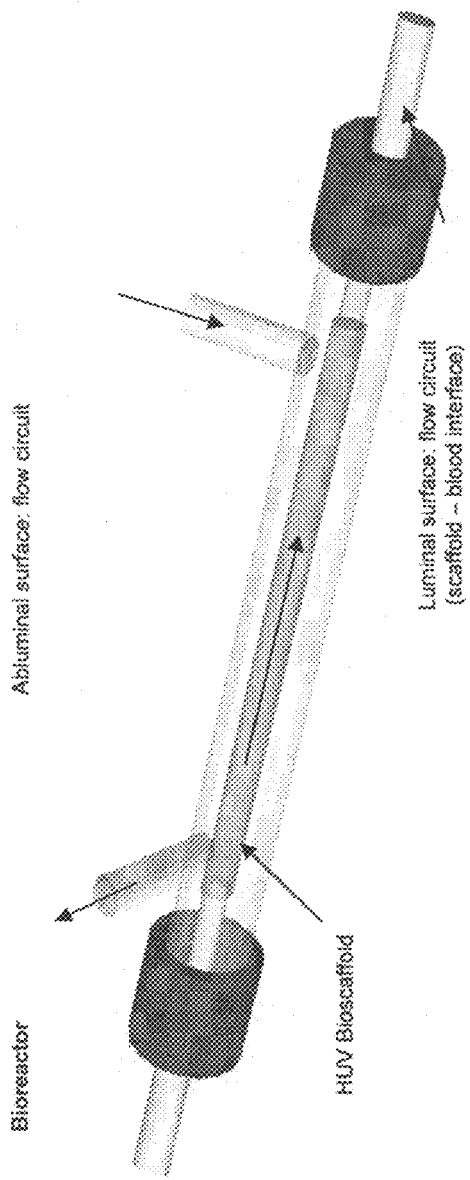
FIG. 18 graphically illustrates a bioreactor body of the prior art that could be used to connect to the process flow circuit of FIG. 17. By increasing the pressure within the luminal flow circuit radial strain results in mechanical shear cells imbedded within the scaffold.

Bioreactor and process flow design. The bioreactor body is constructed of glass tubing, (OD) 10 mm (ID) 8 mm×180 mm long, with a total reactor volume of 9.1 cm$^3$. Quick-fit 10/4 threaded tube with complementary screw-cap couplings attach to the reactors main body. The stainless steel adaptors pass (and seal) through the bioreactor endcaps connecting the HUV scaffold to the tubing of the flow circuit (FIG. 18).

To ensure flow into the reactor is within the laminar flow range, the Reynolds number ($N_{Re}$) was calculated using the test conditions above (Best et al., 1991)

$$N_{Re} = \frac{\rho u d}{\mu}(1.0)$$

where d=vessel diameter, u=velocity, ρ=density and μ=viscosity. It is generally accepted that as the calculated Reynolds number increases over 2300, there is a transition from laminar to turbulent flow. Fluid viscosity (μ) is assumed to be the same as water at 20° C. The Reynolds numbers for the two conditions set where: 1. artery mean diameter 3 mm, 2. 3.2 mm stainless steel, were $N_{Re}$=987, and 801 respectively, both well within the laminar range. The process flow is designed to operate in concert with the bioreactor to deliver media to the cellular population/s within the matrix under pulsatile flow conditions. The media reservoir (100 ml capacity), has a media pick-up and return lines, with a third port for connected to 0.2 μm filter to allow for atmospheric gas exchange (5% $CO_2$+air). Media is drawn and pulsed by a MasterFlex L/L computerized drive with a 7725-62 pumphead from the media storage vessel into a compliance chamber, then through the bioreactor and recirculating back to the media vessel. Two separate pumps and media vessels operate in unison to deliver media and the applied mechanical forces to the two different surfaces of the construct. All system tubing consists of silicone tubing 4.8 mm ID, 8 mm OD, with the exception of PharMed medical grade peristaltic tubing around the pump head.

Figure 12:
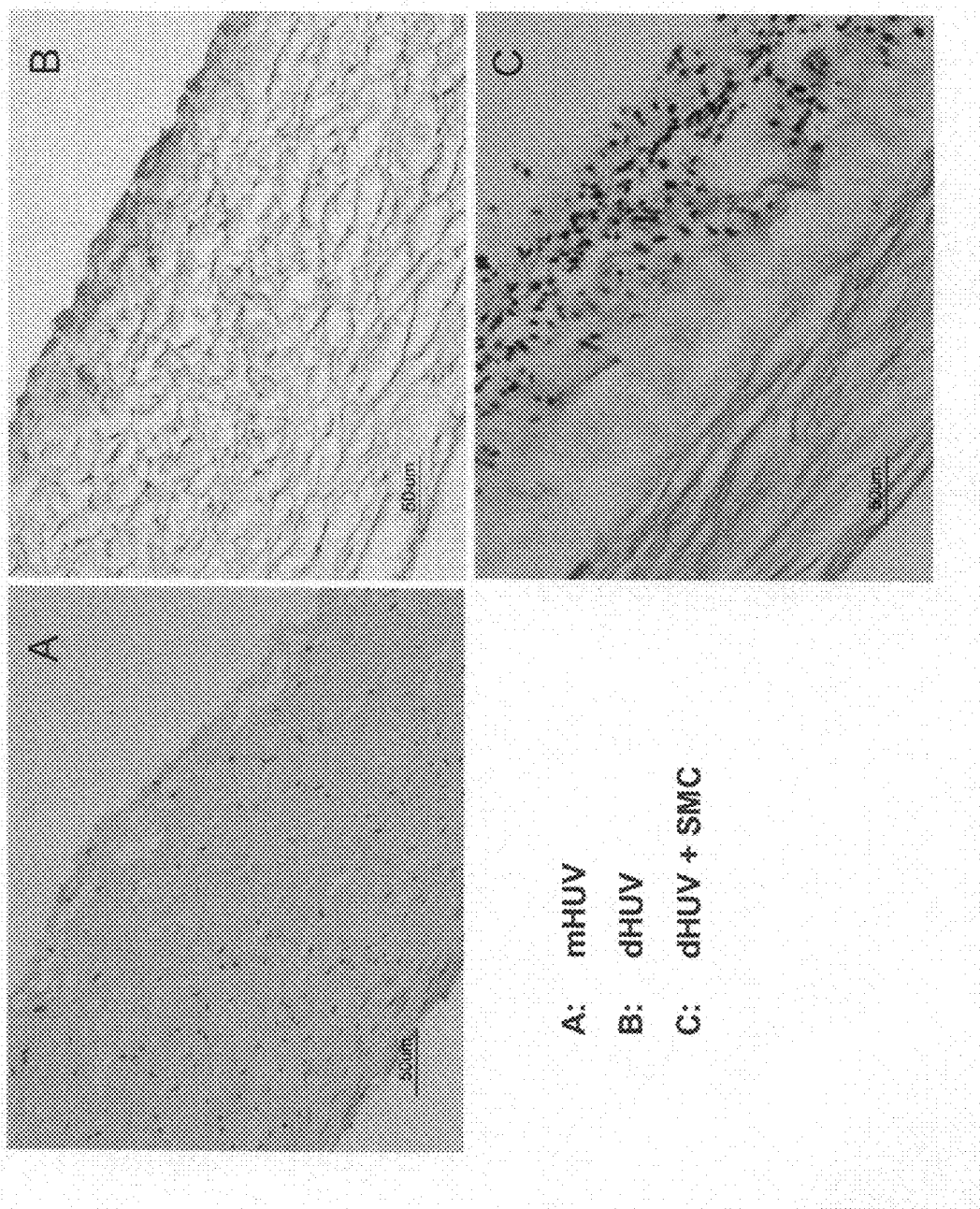
FIG. 12 contains photographs of histological images of native HUV (upper left), and the native HUV decellularized (upper right). Primary human SMC are seeded onto the ablumenal surface of the decellularized HUV and visualized by H&E (lower right), thereby illustrating cellular attachment.
Figure 19:
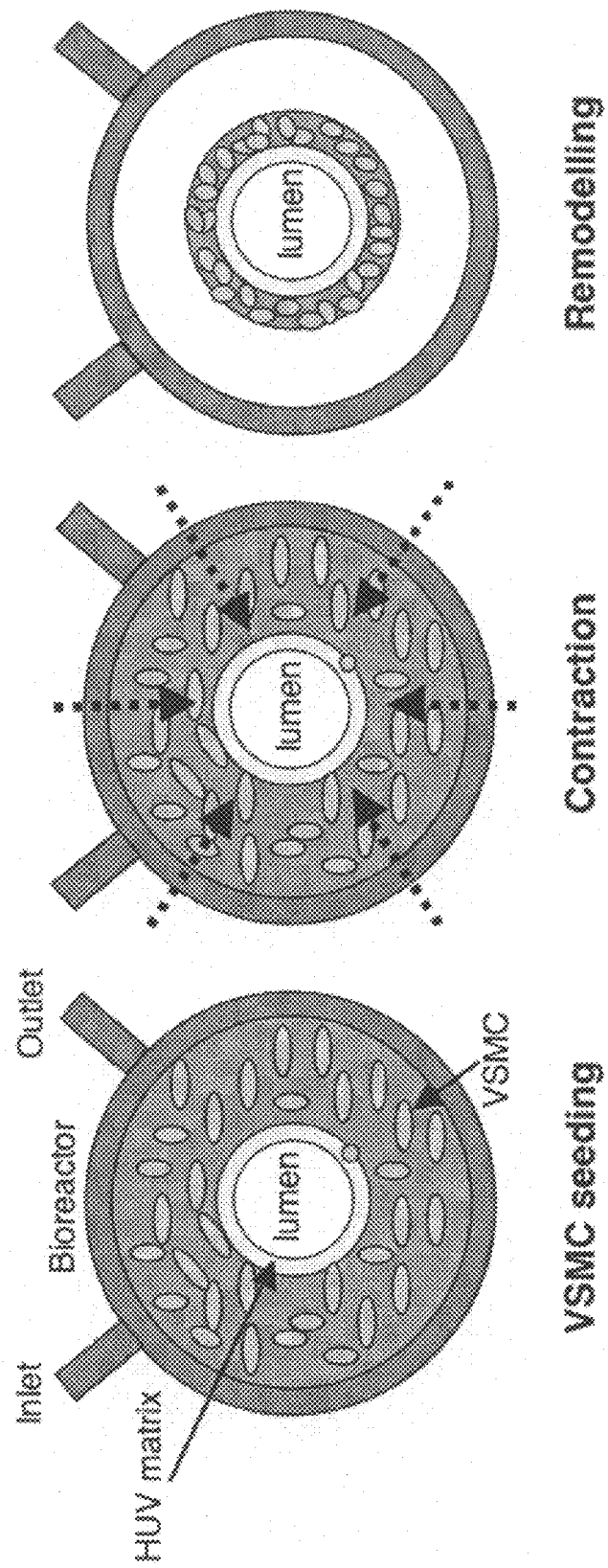
FIG. 19 graphically illustrates cross-sectional views of the vascular bioreactor of FIG. 18 having a HUV disposed therein and cell seeded thereon in accordance with the methods of the present invention. The collagen hydrogel/vascular smooth muscle cell (VSMC) suspension is loaded and allowed to polymerize (left). The hydrogel begins contraction around the HUV (approximately day 1 through day 5, depending on cell/gel concentration). Over time VSMC remodel the collagen gel/HUV matrix into a functional vessel wall (right).
Figure 20:
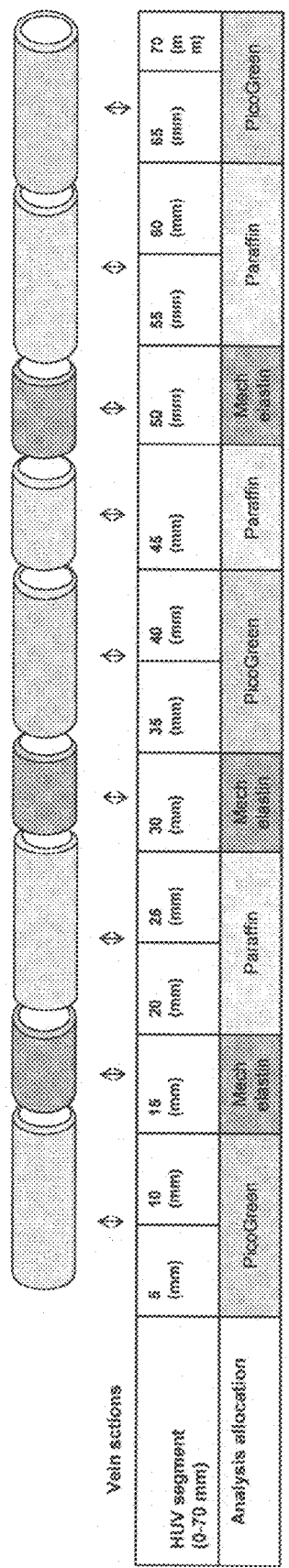
FIG. 20 graphically illustrates how a 70 mm long sample of HUV is divided into 14 longitudinal subsections at 5 mm intervals for analysis: mechanical analysis (Mech), PicoGreen DNA quantification (PG), and paraffin embedded sections for determination of viable cells, migration analysis, and scaffold remodeling.

Cell seeding using the collagen hydrogel cell-delivery system. In order to maintain consistency between the bioreactor and static based cultures the same seeding method was employed. This method supersedes the method described in a recent publication from our labs using cell-sheets to wrap cells around the 3D surface (McFetridge et al., 2004). Due to the 3D nature of tubular scaffolds it is technically challenging to seed the surface of the scaffold with a high density of cells in a uniform layer. To over come this problem, the abluminal void of the bioreactor was inoculated with collagen hydrogel/cell suspensions and allowed to polymerize. Over a period of 24-48 hours the gel contracts off the inner wall of the bioreactor and 'shrink-wraps' around the scaffold that is suspended in the middle of the bioreactor (FIG. 19). Using this method, uniform layers of cells are achieved, where the collagen gel is largely absorbed into the scaffold. FIG. 12 shows an H&E section of cells seeded onto the HUV using this technique. Hydrogels are made on ice to a final concentration of 1.25 mg/ml bovine type I collagen (Invitrogen, Inc.) with a cell density $8.1 \times 10^5$ cell/ml.

Cell density/collagen volume is adjusted to maintain consistency between the two culture systems. After gel/cell inoculation into the bioreactor, the gel polymerizes at 37° C. (0.04% $CO_2$) to maintain the pH at 7.2. After 1 hour constructs are transferred to the tissue culture incubator (37° C. 5% $CO_2$) for a further 24 hours before the abluminal ports are opened and media perfused (1 ml/min) for the experimental duration.

Histology and immunohistochemistry. All HUV sections are fixed in formal saline and paraffin embedded. Sections are cut to 5 μm thickness, mounted on glass slides and baked at 65° C. for 12 hours. Slides are then dewaxed and rehydrated. Hemotoxylin staining follows standard protocols. For immunohistochemistry, slides are then incubated in blocking solution (0.5 mg bovine serum albumin, 333 μl FCS, 10 ml PBS) for 20 minutes at room temperature. The blocking solution is then removed, and the primary antibody is applied and incubated at 4° C. overnight. Slides are washed in PBS, followed by incubation in the appropriate fluorescently tagged secondary antibody made up in blocking solution for 30 minutes at room temperature. Finally the slides are washed (2×5 minutes) in PBS and mounted using fluorescent mounting medium. Primary antibodies: MMP-1 mouse anti-human-MMP-1 monoclonal antibody (Cat. MAB3307 Chemicon); MMP-2 mouse anti-human-MMP-2 monoclonal antibody (Cat. MAB3308 Chemicon); MMP-8 mouse anti-human-MMP-8 polyclonal antibody (Cat. AB8115 Chemicon); MMP-9 mouse anti-human-MMP-9 monoclonal antibody (Cat. MAB3309 Chemicon); human procollagen-1 rat anti human procollagen-1 monoclonal antibody (cat. MAB1912). Secondary antibodies: Mouse anti-goat rhodamine conjugated secondary antibody (100:1 dilution) (Cat, AP300R Chemicon) MMP-1, 2, 8, 9. Procollagen-1 is a horse-anti-mouse-FITC conjugate in a 1:100 dilution (Cat, 5024 Chemicon). Visualization of all matrix and fluorescent images were carried out using a Nikon E800 epiflorescent microscope at the appropriate wave length.

Pico-Green DNA quantification: Although this is not a direct measure of cell viability this assay confirms whether or not an increase in population density is occurring, thus indirectly measuring viability. Triplicate samples were assessed at days 1, 5, 10, 20, and 30 to quantify total cell density using the PicoGreen assay within the tissue constructs over time. Working solutions of the PicoGreen reagent (1:200 dilution) are made up in concentrated DMSO solution in 10 mM Tris-HCl, 1 mM EDTA, pH 7.5 (TE). Using known concentrations of hVSMC a calibration curve is first completed by preparing a 2 μg/mL stock solution of dsDNA in TE. DNA concentration is based on absorbance at 260 nm (A260; an A260 of 0.04 corresponds to 2 μg/mL dsDNA solution). Table 2 describes the single-replicate, five-point standard curve made from 1 ng/mL to 1000 ng/mL of dsDNA. Segments of the HUV scaffold dissected according to the allocation described above, weighed, then incubated in a collagenase solution (1:5 w/v) for 2 hours at 37° C. Samples are then placed in a mortar and ground until a slurry in produced. The total solution is then centrifuged at 200 g for 2 minutes to pellet bulk ECM components. The total DNA is then purified by precipitation in an alcohol/water mixture in the presence of a high concentration of inorganic salt. DNA is recovered from the aqueous solution by addition of salt to final concentrations of 0.8M LiCl, 0.4M NaCl, and NaOAc and an appropriate volume of alcohol (30% isopropanol; 70% ethanol). The sample is then stored for 30 minutes at −20° C., and then allowed to warm to 0° C. The solution is subjected to centrifugation at 9300 g, then desalted by rinsing in 70% alcohol, followed by recentrifugation. Samples are then incubated (as above) with the PicoGreen reagent, and sample fluorescence is measured 260 nm. The fluorescence value of the reagent with control samples (no seeded cells) is subtracted from that of each sample to yield fluorescence versus DNA concentration.

Elastin content/structure: Elastin content was assessed using Fastin, a dye label 5,10,15,20-tetraphenyl-21,23-porphine sulfonate, that specifically binds elastin. Samples designated for mechanical analysis were solubilized after mechanical testing using oxalic acid to quantify elastin deposition at an absorbance of 513 nm. Verhoeff's Van Gieson elastin stain was used to assess elastin histology.

Cell viability: The addition of complexed BrUTP-FuGENE 6 to cell cultures makes it possible to demonstrate active transcription. The brominated RNA (BrU-RNA) is immunodetected by fluorescence microscopy using an antibody to bromodeoxyuridine. With the method, no incorporation of BrUTP into DNA is recorded (Jackson et al., 1993; and Wansink et al., 1993). As apoptotic cells produce significantly less mRNA and the mRNA in necrotic cells is rapidly degraded by Rnase, viable cells can be clearly discerned from non-viable cells.

TABLE 2

Protocol for preparing standard curve.

| Volume (μL) 2 μg/ml DNA | Volume (μL) TE | Volume (μL) PicoGreen | DNA Concentration in PicoGreen Assay |
|---|---|---|---|
| 1000 | 0 | 1000 | 1000 ng/ml |
| 500 | 500 | 1000 | 500 ng/ml |
| 100 | 900 | 1000 | 100 ng/ml |
| 10 | 990 | 1000 | 10 ng/ml |
| 1 | 999 | 1000 | 1 ng/ml |
| 0 | 1000 | 1000 | Blank |

In addition, using controls to show the level of binding in chemically induced apoptotic cells (500 ng/ml of actinomycin D) is significantly reduced, allows determination of apoptotic verses live and non-viable cells.

The BrUTP/FuGENE 6 mixture is mixed by gently tapping the tube and left at room temperature for 15 min for complexing. The complex is then inoculated into the abluminal void of the bioreactors and maintained for 60 at 4° C., then rinsed in PBS at 37° C. followed by reinitiating the media flow for various pulse periods at 37° C. before being processed for immunofluorescence analysis. After chasing with BrUTP-FuGENE 6, cultures are fixed with 3.7% formal saline and paraffin embedded for immunofluorescence analysis. Sections are dewaxed with zylene and rehydrated. Coverslips are treated with 0.5% bovine serum albumin in PBS for 15 min to avoid non-specific binding of immunoglobulins. A primary antibody for detection of BrU-RNA using a mouse monoclonal IgG-1 antibody raised against 5-bromo-2'-deoxyuridine-5-monophosphate (Anti-bromodeoxyuridine™, Boehringer Mannheim, Clone BMC 9318) was used. Cells are incubated with primary antibody overnight at 4° C. followed by washings and treatment with goat anti-mouse IgG-1 FITC conjugate (Southern Biotechnology, AL, USA) for 60 min at room temperature for anti-BrdU. As a control, cells will be processed for immunofluorescence with the omission of the primary antibody incubation step. Cell populations were counter stained with the blue-fluorescent dye Hoechst 33342 (Molecular Probes) to screen the total cell number.

Image analysis for the quantification of cell migration: Cell migration index. Cross sectional images of tissue samples with seeded cells were obtained as described above. The cell nuclei are stained with haematoxylin to delineate them from surrounding tissue. The preparations are examined by a Nikon E800 upright microscope connected to a Nikon 1200 cooled CCD with controller unit. Images will be captured by a frame grabber unit and stored. Several different quantitative measures of the extent of cell migration into the scaffold material were obtained. These include the total number of cells that have migrated into the material, the average distance of migration into the material, and the variance of the migration distance. Images are digitized and analyzed with a using the image analysis software package by Metamorph, v6.2 (Universal Imaging Corporation). Cells are identified by the software with the aid of two adjustable parameters, the intensity of the stained nuclei and their size. The intensity parameter allows an upper and a lower bound on the intensity of the objects of interest (in this case the cell nuclei) to be specified, while the size parameter allows the size (in terms of the number of continuous pixels) of the object of interest to be specified. Once individual cells are identified, the software computes the centroid of each cell. The software then allows the distance from the centroid to a line drawn on the image that indicates the edge of the scaffold to be computed. These distance measures for each cell are then exported to Microsoft Excel where the statistical analysis is performed to quantify the total number of cells that have migrated into the material, the average distance of migration into the material, and the variance of the migration distance over time.

Cell remodeling MMP 1, 2, 8, 9, and procollagen-1: The histological evaluation of cell remodeling activity assesses expression of matrix metalloprotease 2, 13, and expression of the procollagen-1. Samples obtained over the experimental duration (days 1, 5, 10, 20 and 30) are fluorescently labelled to identify expression of these key remodeling enzymes and markers of collagen synthesis. Each triplicate set of HUV samples have three tissue samples embedded in paraffin, from each three 5 µm histological sections will be cut for analysis. Preparations are examined using a Nikon E800 microscope connected to a Nikon 1200 cooled CCD with controller unit. Images are captured by a frame grabber unit and stored. Image analysis software, Metamorph, v6.2 (Universal Imaging Corporation), is calibrated to view matrix sections 625× 400 mm (0.25 mm$^2$) labelled antibodies are then quantified to determine the percentage area. This data is then used as a comparative assessment between time points, markers (MMP-2,13 and procollagen-1), and the variable between each specific aim.

Mechanical analysis: A uniaxial tensile testing (United Testing Systems, Inc., Model SSTM-2K, Flint, Mich.) is used to determine the stress-strain relationship, Young's modulus, and yield stress. Circular vein samples are cut to 5 mm wide ringlets then cut to form a strip of tissue 5 mm wide×12 mm long and inserted into standard tissue grips (McFetridge et al., 2004; and Hiles et al., 1995). Samples are preloaded to a stress of 0.5 g at a rate of 5 mm/min (McFetridge et al., 2004; and Courtman et al., 1995). Using the same extension rate 5 mm/min samples are then stressed until failure (McFetridge et al., 2004). Suture holding capacity is assessed using the same uniaxial tensile test rig and above to apply uniaxial stress to the sutured samples. Vein sections were cut longitudinally to make a flat sheet approximately 15 mm wide by 80 mm in length. Using tissue clamps, samples are attached via a single sterile 3-0 braided silk suture (Henry Schein, Melville, N.Y.). Sutures are passed through the non-clamped distal/proximal end of the vessel 2 mm below the cut edge (Billiar et al., 2001). The suture is then looped and attached to the upper tissue clamp. Samples are preloaded to 0.5 g stress (5 mm/min), and data is recorded at an extension rate of 125 mm/min until tissue failure (Billiar et al., 2001).

Thus, in accordance with the present invention, there has been provided a method for preparing a tubular scaffold for guided tissue regeneration using a human umbilical vessel that has not been substantially cross-linked. Although the invention has been described in conjunction with the specific drawings, experimentation, results and language set forth herein above, it is evident that many alternatives, modifications, and variations will be apparent to those skilled in the art. Accordingly, it is intended to embrace all such alternatives, modifications and variations that fall within the spirit and broad scope of the invention.

REFERENCES

The following references, to the extent that they provide exemplary procedural or other details supplementary to those set forth herein, are specifically incorporated herein by reference in their entirety as though set forth herein particular.

1. Arndt J O, Klauske J, et al.: The diameter of the intact carotid artery in man and its change with pulse pressure. *Pflugers Arch Gesamte Physiol Menschen Tiere* 301: 230-40, 1968.
2. Bader A, Schilling T, et al.: Tissue engineering of heart valves—human endothelial cell seeding of detergent acellularized porcine valves. *Eur J Cardiothorac Surg* 14: 279-84, 1998.
3. Badylak S F, Liang A, et al.: Endothelial cell adherence to small intestinal submucosa: an acellular bioscaffold. *Biomaterials* 20: 2257-2263, 1999.
4. Badylak S F, Record R, et al.: Small intestinal submucosa: a substrate for in vitro cell growth. *Journal of Biomaterial Science. Polymer edition* 9: 863-878, 1998.
5. Badylak S F: Xenogeneic extracellular matrix as a scaffold for tissue reconstruction. *Transplant Immunology* 12: 367-77, 2004.
6. Best C H, Taylor N B. Best and Taylors physiological basis of medical practice. Baltimore, Md. 21202, USA: Williams and Wilkins; 1991.
7. Billiar K, Murray J, et al.: Effects of carbodiimide crosslinking conditions on the physical properties of laminated intestinal submucosa. *Journal of Biomedical Materials Research* 56: 101-8, 2001.
8. Bodnar E, Olsen E G J, et al.: Damage of porcine aortic valve tissue caused by the surfactant sodiumdodecylsulphate. *Thoracic cardiovascular Surgeon* 34: 82-85, 1986.
9. Bouachour G, Cronier P, Gouello J P, Toulemonde J L, Talha A, Alquier P. Hyperbaric oxygen therapy in the management of crush injuries: a randomized double-blind placebo-controlled clinical trial. J Trauma 1996; 41(2):333-9.
10. Budd J S, Allen K E, et al.: The effect of preformed confluent endothelial cell monolayers on the patency and thrombogenicity of small calibre vascular grafts. *European Journal of Vascular Surgery* 5: 397-405, 1991.
11. Bujan J, Pascual G, et al.: Rapid thawing increases the fragility of the cryopreserved arterial wall. *European Journal of Vascular & Endovascular Surgery* 20: 13-20, 2000.
12. Caffesse R G, Mota L F, Quinones C R, Morrison E C. Clinical comparison of resorbable and non-resorbable barriers for guided periodontal tissue regeneration. J Clin Periodontol 1997; 24(10):747-52.
13. Campbell J H, Efendy J L, et al.: Novel vascular graft grown within recipient's own peritoneal cavity. Circ Res 85: 1173-8, 1999.
14. Chen M K, Badylak S F: Small bowel tissue engineering using small intestinal submucosa as a scaffold. *J Surg Res* 99: 352-8, 2001.
15. Courtman D W, Errett B, et al.: The role of cross-linking in modification of the immune response elicited against xenogenic vascular acellular matrices. *Journal of Biomedical Materials Research* 55: 576-586, 2001.
16. Courtman D W, Pereira C A, et al.: Development of a pericardial acellular matrix biomaterial: biochemical and mechanical effects of cell extraction. *Journal of Biomedical Materials Research* 28: 655-666, 1994.

17. Courtman D W, Pereira C A, et al.: Biomechanical and ultrastructural comparison of cryopreservation and a novel cellular extraction of porcine aortic valve leaflets. *Journal of Biomedical Materials Research* 29: 1507-16, 1995.
18. Daniel J, Abe K, McFetridge P S. Automated Dissection of Human Umbilical Cord for Use in Cardiovascular Tissue Engineering. 2004; Austin, Tex., USA.
19. Daniel J, Abe K, McFetridge P S. Development of the human umbilical vein scaffold for cardiovascular applications. ASAIO J. 2004; Under review.
20. Daniel J, McFetridge P S. Preparation of the Human Umbilical Vein for Vascular Tissue Engineering Applications. 2004; Savannah, Ga., USA.
21. Dardik H, Ibrahim I M, et al.: Human umbilical cord. A new source for vascular prosthesis. *Jama* 236: 2859-62, 1976.
22. Dardik H, et al.: Biodegradation and aneurysm formation in umbilical vein grafts. Observations and a realistic strategy. *Ann Surg*, 199(1): 61-68, 1984.
23. Dardik H, Miller N, et al.: A decade of experience with the glutaraldehyde-tanned human umbilical cord vein graft for revascularization of the lower limb. *J Vasc Surg* 7: 336-46, 1988.
24. Dardik H: Human umbilical vein grafts. *Can J Surg*, 33(3): 173-174, 1990.
25. Dardik H: The second decade of experience with the umbilical vein graft for lower-limb revascularization. *Cardiovasc Surg* 3: 265-9, 1995.
26. Dardik H: Regarding "a comparative evaluation of polytetrafluoroethylene, umbilical vein, and saphenous vein bypass grafts for femoral-popliteal above-knee revascularization: a prospective randomized Department of Veterans Affairs cooperative study". *J Vasc Surg* 33: 658-9, 2001.
27. Dardik H D, Ibrahim I M, et al.,: Clinical experience with modified human umbilical cord vein for arterial bypass. *Surgery* 79: 618-24, 1976.
28. Dardik I, Dardik H: Vascular heterograft: human umbilical cord vein as an aortic substitute in baboon. A preliminary report. *J Med Primatol* 2: 296-301, 1973.
29. Davies M G, Hagen P O: Structural and functional consequences of bypass grafting with autologous vein. *Cryobiology*, 31(1): 63-70, 1994.
30. Deutsch M, Meinhart J, et al.: Clinical autologous in vitro endothelialization of infrainguinal ePTFE grafts in 100 patients: a 9-year experience. *Surgery* 126: 847-55, 1999.
31. Dresdale A R, Paone G, Silverman N A: Technical considerations in aortocoronary bypass grafting. *Biomed Pharmacother* 44(7): 359-364, 1990.
32. Eickhoff H, et al.: Four years' results of a prospective, randomized clinical trial comparing polytetrafluoroethylene and modified human umbilical vein for below-knee femoropopliteal bypass. *Journal of Vascular Surgery*, 6(5): 505-511, 1987.
33. Eickholz P, Kim T S, Holle R. Guided tissue regeneration with non-resorbable and biodegradable barriers: 6 months results. *J Clin Periodontol* 1997; 24(2):92-101.
34. Francis K, Palsson B O: Effective intercellular communication distances are determined by the relative time constants for cyto/chemokine secretion and diffusuion. *Proc. Natl. Acad. Sci.* 94:12258-12262, 1997.
35. Feeley T W. Anesthesia. New York: Churchill Livingstone; 1994. 2307-2325.
36. Fujitani R M, et al.: Cryopreserved saphenous vein allogenic homografts: an alternative conduit in lower extremity arterial reconstruction in infected fields. *J Vasc Surg*, 15(3): 519-526, 1992.
37. Gamba P G, Conconi M T, et al.: Experimental abdominal wall defect repaired with acellular matrix. *Pediatr Surg Int* 18: 327-31, 2002.
38. Goissis G, Suzigan S, et al.: Preparation and characterization of collagen-elastin matrices from blood vessels intended as small diameter vascular grafts. *Artificial Organs* 24: 217-223, 2000.
39. Gottlow J. Guided tissue regeneration using bioresorbable and non-resorbable devices: initial healing and long-term results. J Periodontol 1993; 64(11 Suppl):1157-65.
40. Hasson J E, Newton W D, et al.: Mural degeneration in the glutaraldehyde-tanned umbilical vein graft: incidence and implications. *Journal of Vascular Surgery* 4: 243-50, 1986.
41. Hiles M C, Badylak S F, et al.: Mechanical properties of xenogenic small-intestinal submucosa when used as an aortic graft in the dog. *Journal of Biomedical Materials Research* 29: 883-891, 1995.
42. Hodde J P, Record R D, Tullius R S, Badylak S F. Retention of endothelial cell adherence to porcine-derived extracellular matrix after disinfection and sterilization. Tissue Eng 2002; 8(2):225-34.
43. Hoerstrup S P, Zund G, et al.: Tissue engineering of small caliber vascular grafts *European Journal of Cardio-Thoracic Surgery* 20: 164-9, 2001.
44. Hung S L, Lin Y W, Wang Y H, Chen Y T, Su C Y, Ling L J. Permeability of *Streptococcus mutans* and *Actinobacillus actinomycetemcomitans* Through guided tissue regeneration membranes and their effects on attachment of periodontal ligament cells. J Periodontol 2002; 73(8):843-51.
45. Huynh T, Abraham G, et al.: Remodeling of an acellular collagen graft into a physiologically responsive neovessel. *Nature Biotechnology* 17: 1083-6, 1999.
46. Jackson D A, Hassan A B, Errington R J, Cook P R. Visualization of focal sites of transcription within human nuclei. Embo J 1993; 12(3):1059-65.
47. Jepsen S, Heinz B, Kermanie M A, Jepsen K. Evaluation of a new bioabsorbable barrier for recession therapy: a feasibility study. J Periodontol 2000; 71(9):1433-40.
48. Johnson W C, Lee K K: A comparative evaluation of polytetrafluoroethylene, umbilical vein, and saphenous vein bypass grafts for femoral-popliteal above-knee revascularization: A prospective randomized Department of Veterans Affairs cooperative study. *Journal of Vascular Surgery* 32: 268-277, 2000.
49. Kadner A, Zund G, et al.: Human umbilical cord cells for cardiovascular tissue engineering: a comparative study. *European Journal of Cardio-Thoracic Surgery* 25: 635-41, 2004.
50. Karkow W S, et al.: Extended study of aneurysm formation in umbilical vein grafts. Journal of Fascular Surgery 4(5): 486-492, 1986.
51. Khor E: Methods for the treatment of collagenous tissues for bioprostheses. *Biomaterials* 18: 95-105, 1997.
52. Kim B S, Nikoloviski J, Bonadio J, Mooney D J. Cyclic mechanical strain regulates the development of engineered smooth muscle tissue. Nature Biotechnology 1999; 17(October):979-983.
53. Kim B S, Mooney D J. Scaffolds for engineering smooth muscle under cyclic mechanical strain conditions. J Biomech Eng 2000; 122(3):210-5.
54. Kirschenlohr H L, Metcalfe J C, Grainger D J. Cultures of proliferating vascular smooth muscle cells from adult human aorta. In: Jones G E, editor. Methods in Molecular Medicine. Towowa: Humana Press; 1996. p 319-334.
55. Kwon T G, Yoo J J, et al.: Autologous penile corpora cavernosa replacement using tissue engineering techniques. *Journal of Urology* 168: 1754-8, 2002.

56. Langer R: Tissue engineering. *Molecular Therapy* 1: 12-15, 2000.
57. Lantz G C, Badylak S F, et al.: Small intestinal submucosa as a vascular graft: a review. *J Invest Surg* 6: 297-310, 1993.
58. L'Heureux N, Paquet S, et al.: A completely biological tissue-engineered human blood vessel. *FASEB Journal* 12: 47-56, 1998.
59. L'Heureux N, Germain L, and Auger F A: Tissue engineering. Science 284(5420): 1621-1622, 1999.
60. Lin S J, Hou L T, Liu C M, Liao C S, Wong M Y, Ho J Y, Chang W K. Bacterial morphotypes and early cellular responses in clinically infected and non-infected sites after combination therapy of guided tissue regeneration and allograft. J Dent 2000; 28(3):199-206.
61. Malone J, Brendel K, et al.: Detergent-extracted small-diameter vascular prostheses. *Journal of Vascular Surgery* 1: 181-191, 1984.
62. Mathieu D, Wattel F, Bouachour G, Billard V, Defoin J F. Post-traumatic limb ischemia: prediction of final outcome by transcutaneous oxygen measurements in hyperbaric oxygen. J Trauma 1990; 30(3):307-14.
63. McFetridge P S: *Tissue engineering small diameter vascular grafts (PhD thesis)*. Bath, University of Bath, 2002, 301 p.
64. McFetridge P S, Bodamyali T, Chaudhuri J B, Horrocks M. Endothelial and Smooth Muscle Cell Seeding onto Processed ex vivo Arterial Scaffolds using 3D Vascular Bioreactors. ASAIO J 2004; 50(6):591-600.
65. McFetridge P S, Daniel J W, et al.: Preparation of porcine carotid arteries for vascular tissue engineering applications. *Journal of Biomedical Materials Research* 70A: 224-34, 2004.
66. McFetridge P S; Tissue Engineering Vascular Grafts using the Umbilical Vein as a Decellularised Matrix and a Rapid Bioreactor-Based Autologus Seeding Technology for Bypass Surgery. Provisional Application: 60/551,607. USA. 2004 Mar. 9, 2004.
67. Mechanic G L: Cross-linking collagenous product, Chapel Hill, N.C., USA, University of North Carolina, U.S. Pat. No. 5,332,475. 1992.
68. Minabe M. A critical review of the biologic rationale for guided tissue regeneration. J Periodontol 1991; 62(3):171-9.
69. Miyata T, Tada Y, et al.: A clinicopathologic study of aneurysm formation of glutaraldehyde-tanned human umbilical vein grafts. *Journal of Vascular Surgery* 10: 605-611, 1989.
70. Murphy K G. Postoperative healing complications associated with Gore-Tex Periodontal Material. Part I. Incidence and characterization. Int J Periodontics Restorative Dent 1995; 15(4):363-75.
71. Nerem R M: Tissue engineering a blood vessel substitute: the role of biomechanics. *Yonsei Medical Journal* 41: 735-9, 2000.
72. Nerem R M, Seliktar D: Vascular Tissue Engineering. *Annual Review of Biomedical Engineering* 3: 225-243, 2001.
73. Nevelsteen A, et al.: Intravenous digital subtraction angiography and Duplex scanning in the detection of late human umbilical vein degeneration. British Journal of Surgery 75(7): 668-670, 1988.
74. Niklason L E, Langer R S: Advances in tissue engineering of blood vessels and other tissues. *Transplant Immunology* 5: 303-6, 1997.
75. Niklason L E, Gao J, et al.: Functional arteries grown in vitro. *Science* 284: 489-493, 1999.
76. Niklason L E, et al.: Morphologic and mechanical charactistics of engineered bovine arteries. Journal of Vascular Surgery 33: 628-638, 2001.
77. Oegema T R, Jr., Deloria L B, et al.: A simple cryopreservation method for the maintenance of cell viability and mechanical integrity of a cultured cartilage analog. *Cryobiology* 40: 370-5, 2000.
78. Oliver R F, Grant R A: Implant Tissue, *World Intellectual Property Organisation, UK, Oliver, R. F.,* 1985, pp. 1-22.
79. Ozawa T, Mickle D A, Weisel R D, Koyama N, Ozawa S, Li R K. Optimal biomaterial for creation of autologous cardiac grafts. Circulation 2002; 106(12 Suppl 1):I176-82.
80. Pegg D E, Wusteman M C, et al.: Fractures in cryopreserved elastic arteries. *Cryobiology* 34: 183-92, 1997.
81. Perry R H, Green D W. Perry's Chemical Engineers Handbook: McGraw-Hill International Editions, Chemical Engineering Series; 1998.
82. Probst M, Dahiya R, et al.: Reproduction of functional smooth muscle tissue and partial bladder replacement. *British Journal of Urology* 79: 505-515, 1997.
83. Probst M, Piechota H J, et al.: Homologous bladder augmentation in dog with the bladder acellular matrix graft. British Journal of Urology 85: 362-371, 2000.
84. Rachlin G, Koubi G, Dejou J, Franquin J C. The use of a resorbable membrane in mucogingival surgery. Case series. J Periodontol 1996; 67(6):621-6.
85. Reid L C, Rojkind M: Method for the isolation of connective tissue biomatrix, USA, Albert Einstein College of Medicine of Yeshiva University, Bronx, N.Y., 1987.
86. Roeder R, Wolfe J, et al.: Compliance, elastic modulus, and burst pressure of small-intestine submucosa (SIS), small-diameter vascular grafts. *Journal of Biomedical Materials Research* 47: 65-70, 1999.
87. Saito M, Takenouchi Y, et al.: Complete primary structure of rainbow trout type I collagen consisting of alpha1(I) alpha2(I)alpha3(I) heterotrimers. *European Journal of Biochemistry* 268: 2817-27, 2001.
88. Sawyer P (ed): *Modern Vascular Grafts*. New York, McGraw-Hill, Inc., 1987.
89. Schaner P J, Martin N D, et al.: Decellularized vein as a potential scaffold for vascular tissue engineering. *Journal of Vascular Surgery* 40: 146-53, 2004.
90. Schmidt S P, Bowlin G L: Endothelial cell seeding: A review, in Zilla P, Greisler H P (eds), *Tissue Engineering of Vascular Prosthetic Grafts*, Austin, R.G. Lanes Company, 1999, pp. 61-67.
91. Schmidt C E, Baier J M: Acellular vascular tissues: natural biomaterials for tissue repair and tissue engineering. *Biomaterials* 21: 2214-2231, 2000.
92. Seifalian A M, Giudiceandrea A, et al.: Non-compliannce: The silent acceptance of a villain, in Zilla P, Greisler H P (eds), *Tissue engineering of vascular prosthetic grafts*, Austin, R.G. Landers Company, 1999, pp. 621.
93. Seliktar D, Black R A, Vito R P, Nerem R M. Dynamic mechanical conditioning of collagen-gel blood vessel constructs induces remodeling in vitro. Ann Biomed Eng 2000; 28(4):351-62.
94. Seliktar D, Nerem R M, Galis Z S. The role of Matrix Metalloproteinase-2 in the remodelling of Cell Seeded Vascular Constructs Subjected to Cyclic Strain. Annals of Biomedical Engineering 2001; 29:923-934.
95. Shama F, Sherman P. Identification of stimuli controlling the sensory evaluation of viscosoty. Journal of Texture Studies 1973; 4: 111-118.
96. Tai N R, Salacinski H J, et al.: Compliance properties of conduits used in vascular reconstruction. *Br J Surg* 87: 1516-24, 2000.

97. Tamura N, Terai H, et al.: An "acellular" vascular prosthesis may provide a scaffold for the host tissue regeneration. *International Journal of Artificial Organs* 22: 419 (abstract), 1999.
98. Teebken O E, Bader A, et al.: Tissue engineering of vascular grafts: Human cell seeding of decellularised porcine matrix. *European Journal of Vascular and Endovascular Surgery* 19: 381-386, 2000.
99. Teebken O E, Pichimaier M A, et al.: Cryopreserved arterial allografts for in situ reconstruction of infected arterial vessels. *Eur J Vasc Endovasc Surg* 27: 597-602, 2004.
100. Vyavahare N, Hirsch D, et al.,: Prevention of Bioprosthetic Heart Valve Calcification by Ethanol Preincubation: Efficacy and Mechanisms. *Circulation* 95: 479-488, 1997.
101. Wansink D G, Schul W, van der Kraan I, van Steensel B, van Driel R, de Jong L. Fluorescent labeling of nascent RNA reveals transcription by RNA polymerase 11 in domains scattered throughout the nucleus. J Cell Biol 1993; 122(2):283-93.
102. Watanabe M, et al.: Tissue-engineered vascular autograft:: inferior vena cava replacement in a dog model. Tissue Eng. 74(4): 429-439, 2001.
103. Werkmeister J A, et al.: Evaluation of the Omniflow collagen-polymer vascular prosthesis: immunohistological analysis using monoclonal antibodies. Advances in Science Technology 12:767-776, 1995.

What is claimed is:

1. A process of preparing a decellularized matrix on which at least one cell type may be seeded to remodel a tissue, comprising the steps of:
    providing at least a portion of an umbilical cord;
    isolating an umbilical vessel of the umbilical cord by disposing a mandrel into a lumenal space of the umbilical vessel, wherein the mandrel has a diameter that is equal to or slightly greater than a diameter of the luminal space of the umbilical vessel, and wherein the mandrel is formed of a material having a low coefficient of expansion such that the mandrel does not expand or contract at a rate that is not supportive of the umbilical vessel supported thereon;
    securing the umbilical cord to the mandrel;
    freezing the umbilical cord secured to the mandrel to a temperature in a range of from about −40° C. to about −150° C.;
    automatically dissecting the remainder of the umbilical cord away from the isolated umbilical vessel such that the isolated umbilical vessel has a substantially uniform thickness;
    thawing the isolated, dissected umbilical vessel secured to the mandrel; and
    decellularizing the isolated umbilical vessel while substantially maintaining the structural composition of the extracellular matrix such that the isolated umbilical vessel maintains a surface on which at least one cell type may be seeded and thus allowed to adhere thereto, be maintained thereon and migrate therethrough, and wherein the isolated umbilical vessel is not substantially cross-linked.

2. The process of claim 1 wherein, in the step of decellularizing the isolated umbilical vessel, the isolated umbilical vessel is decellularized by a process selected from the group consisting of washing with hypotonic solution; mechanical removal methods such as cutting, scraping, shaking, and removal by forceps or other suitable instrument; treatment with at least one lipase, at least one protease, at least one nuclease, at least one solvent, and at least one detergent; and combinations thereof.

3. The process of claim 1 wherein, in the step of decellularizing the isolated umbilical vessel, the isolated umbilical vessel is decellularized by a pressure based extraction system with uniform convective flow.

4. The process of claim 1 further comprising the step of unwinding the umbilical cord prior to securing the umbilical cord to the mandrel.

5. The process of claim 1 wherein, in the step of isolating an umbilical vessel, the umbilical vessel is an umbilical vein.

6. The process of claim 5 wherein the umbilical vessel is a mammalian umbilical vein.

7. The process of claim 5 wherein the umbilical vessel is a human umbilical vein.

8. The process of claim 1 wherein the umbilical vessel is an umbilical artery.

9. The process of claim 8 wherein the umbilical vessel is a mammalian umbilical artery.

10. The process of claim 8 wherein the umbilical vessel is a human umbilical artery.

11. The process of claim 1 further comprising the step of seeding at least one cell type on the decellularized umbilical vessel.

12. The process of claim 11 wherein the at least one cell type is selected from the group consisting of smooth muscle cells, fibroblasts, endothelial cells, dendritic cells, keratinocytes, myogenic cells, stem cells, muscle cells, epithelial cells, and combinations thereof.

13. The process of claim 12 wherein the step of seeding at least one cell type is further defined as providing an at least one cell type/collagen gel suspension and seeding the at least one cell type/collagen gel suspension on at least a portion of at least one surface of the decellularized umbilical vessel.

14. The process of claim 13 wherein an endothelial cell/collagen gel suspension is seeded on at least a portion of a lumenal surface of the umbilical vessel.

15. The process of claim 13 wherein an at least one cell type/collagen gel suspension is seeded on at least a portion of an ablumenal surface of the umbilical vessel, and wherein the at least one cell type of the at least one cell type/collagen gel suspension is selected from the group consisting of fibroblasts, smooth muscle cells and combinations thereof.

16. The process of claim 13 wherein a gingival fibroblast/collagen gel suspension is seeded on at least a portion of an ablumenal surface of the umbilical vessel.

17. The process of claim 1 wherein the process further comprises the step of longitudinally dissecting at least a portion of the decellularized umbilical vessel to form a substantially flat sheet of decellularized matrix.

18. The process of claim 1 wherein the step of freezing the umbilical cord secured to the mandrel to a temperature in a range of from about −40° C. to about −150° C. is further defined as freezing the umbilical cord secured to the mandrel to a temperature in a range of from about −60° C. to about −100° C.

19. The process of claim 1 wherein the step of freezing the umbilical cord secured to the mandrel to a temperature in a range of from about −40° C. to about −150° C. is further defined as freezing the umbilical cord secured to the mandrel to a temperature of about −80° C.

20. A process of forming a tissue graft, comprising the steps of:
    providing an acellular tissue graft matrix comprising a decellularized umbilical vessel having a luminal surface and an ablumenal surface, the decellularized umbilical vessel prepared by an automated dissection process whereby the decellularized umbilical vessel is provided with a substantially uniform thickness while substantially maintaining the structural composition of the extracellular matrix such that at least one cell type is capable of adhering thereto, being maintained thereon and migrating therethrough, wherein the decellularized umbilical vessel has not been substantially cross-linked; and implanting the tissue graft in a patient in need thereof.

21. A process of forming a tissue graft having at least one cell type seeded thereon, comprising the steps of:

providing a tissue graft comprising:

a decellularized umbilical vessel having a luminal surface and an ablumenal surface, the decellularized umbilical vessel prepared by an automated dissection process whereby the decellularized umbilical vessel is provided with a substantially uniform thickness while substantially maintaining the structural composition of the extracellular matrix, wherein the decellularized umbilical vessel has not been substantially cross-linked such that the decellularized umbilical vessel is capable of having at least one cell type seeded on at least a portion of at least one of the luminal and ablumenal surfaces thereof and thus allowed to adhere thereto, be maintained thereon and migrate therethrough; and a suspension of collagen gel and at least one cell type, wherein the collagen gel/at least one cell type suspension is seeded upon the decellularized umbilical vessel;

obtaining a tissue biopsy from a patient, wherein the tissue biopsy comprises at least one cell type;

isolating and fractionating the at least one cell type from the tissue biopsy;

mixing the isolated at least one cell type with a collagen gel to provide a collagen gel/cell suspension;

culturing the collagen gel/cell suspension with the tissue graft in a bioreactor under conditions that allow the collagen gel to contract on at least a portion of at least one surface of the tissue graft, thereby seeding the at least one cell type on at least a portion of the tissue graft; and implanting the tissue graft having the collagen gel/cell suspension thereon into the patient.

* * * * *